US008193353B2

(12) United States Patent
Giordani et al.

(10) Patent No.: US 8,193,353 B2
(45) Date of Patent: Jun. 5, 2012

(54) 6-1H-IMIDAZO-QUINAZOLINE AND QUINOLINES DERIVATIVES, NEW POTENT ANALGESICS AND ANTI-INFLAMMATORY AGENTS

(75) Inventors: Antonio Giordani, Pavia (IT); Stefano Mandelli, Casatenovo (IT); Ilario Verpilio, Arluno (IT); Simona Zanzola, Milan (IT); Francesca Tarchino, Varazze (IT); Gianfranco Caselli, Milan (IT); Tiziana Piepoli, Milan (IT); Silvio Mazzari, Padua (IT); Francesco Makovec, Lesmo (IT); Lucio Claudio Rovati, Monza (IT)

(73) Assignee: Rottapharm S.p.A, Milan (IT)

( * ) Notice: Subject to any disclaimer, the term of this patent is extended or adjusted under 35 U.S.C. 154(b) by 0 days.

(21) Appl. No.: 13/169,350

(22) Filed: Jun. 27, 2011

(65) Prior Publication Data
US 2011/0257209 A1    Oct. 20, 2011

Related U.S. Application Data

(62) Division of application No. 12/376,080, filed as application No. PCT/EP2006/065013 on Aug. 3, 2006, now Pat. No. 7,994,181.

(51) Int. Cl.
C07D 239/72    (2006.01)
(52) U.S. Cl. ..................................... 544/284
(58) Field of Classification Search .................. 544/284
See application file for complete search history.

(56) References Cited

U.S. PATENT DOCUMENTS
4,792,561 A    12/1988 Walker et al.

FOREIGN PATENT DOCUMENTS
EP    1 571 142 A1    9/2005
WO    94/22852 A1    10/1994
WO    01/70703 A2    9/2001

OTHER PUBLICATIONS

A. Barrett et al, "An Improved Synthesis of 5,6-trans-Ergocalciferol", Synthesis, Communications, pp. 741-742, 1978.
A. Kiyomori et al, "An Efficient Copper-Catalyzed Coupling of Aryl Halides with Imidazoles", Tetrahedron Letters, vol. 40, pp. 2657-2660, 1999.
A. Shafiee et al, "Synthesis and Antihypertensive Activities of New 1,4-Dihydropyridine Containing Nitroimidazolyl Substituent with a Nitroxy Group at the 3-Ester Position", Arch. Pharm. Pharm. Med. Chem., vol. 2, pp. 59-76, 2002.
A. Shibakawa et al, "Presence of pannus-like tissue on osteoarthritic cartilage and its histological character", Osteoarthritis and Cartilage, vol. 11, pp. 133-140, 2003.
A. West, "Solid State Chemistry and its Applications", Wiley, New York, 1988, pp. 358 and 365.

B. Boyce et al, "Osteoclast precursors: cytokine-stimulated immunomodulators of in", Current Opinion in Rheumatology, vol. 18, Issue 4, pp. 427-432, Jul. 2006.
B. Moller et al, "Inhibition of IL-1, IL-6, and TNF-a in immune-mediated inflammatory diseases", Springer Semin. Immun., vol. 27, pp. 391-408, 2006.
C. Alabaster et al, "2(1H)-Quinolinones with Cardiac Stimulant Activity. 2. Synthesis and Biological Activities of 6-(N-Linked, Five-Membered Heteroaryl) Derivatives", J. Med. Chem., vol. 32, pp. 575-583, 1989.
C. Courteix et al, "Streptozocin-induced diabetic rats: behavioural evidence for a model of chronic pain", Pain, vol. 53, pp. 81-88, 1993.
C. J. Woolf et al, "Cytokines, nerve growth factor and inflammatory hyperalgesia: the contribution of tumour necrosis factor a", British Journal of Pharmacology, vol. 121, pp. 417-424, 1997.
D. Pooranchand et al, "Reaction of Dimethyl N-Aryl- and N-Alkylcarbonimido-dithioates with Aminoacetaldehyde Diethyl Acetal: A Direct Synthesis of 1-Aryl- and 1-Alkyl-2-methylthioimidazoles", Synthesis, Communications, vol. 12, pp. 1136-1138, Dec. 1987.
G. Maga et al, "Specific Targeting of Hepatitis C Virus NS3 RNA Helicase. Discovery of the Potent and Selective Competitive Nucleotide-Mimicking Inhibitor QU663", Biochemistry, vol. 44, pp. 9637-9644, 2005.
I. Antonini et al, "Synthesis of N1-Aryl- and N1-Benzyl Substituted Imidazole-4- and Imidazole-5-carbaldehydes", Synthesis, Communications, pp. 47-49, 1983.
J. Antilla et al, "Copper-Diamine-Catalyzed N-Arylation of Pyrroles, Pyrazoles, Indazoles, Imidazoles, and Triazoles", J. Org. Chem., vol. 69 (17), pp. 5578-5587, 2004.

(Continued)

Primary Examiner — James O Wilson
Assistant Examiner — Brian McDowell
(74) Attorney, Agent, or Firm — Sughrue Mion, PLLC

(57) ABSTRACT

The present invention is directed to novel 6-1H-imidazo-2-aryl and 2-heteroaryl quinazoline and quinoline of formula I, corresponding salts and solvates thereof, to a process for their preparation and to the use of this compounds and corresponding pharmaceutical composition for the treatment of pain and inflammatory related disorders. Compounds of the invention have been proven highly effective in the pharmacological treatment of both inflammatory and neuropathic pain, in addition to striking anti-inflammatory properties. Their effectiveness in interfering with COX-2 and inflammatory cytokines expressions and production, highlights them as interesting compounds also for the treatment of cancer in addition to several inflammatory diseases.

Formula I:

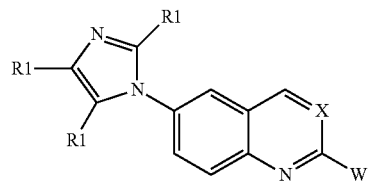

12 Claims, No Drawings

OTHER PUBLICATIONS

J. Duque et al, "Up-regulation of cyclooxygenase-2 by interleukin-1B in colon carcinoma cells", Cellular Signalling, vol. 18, pp. 1262-1269, 2006.
J. H. Chang et al, "Efficient Synthesis of 1-Substituted-5-Hydroxymethylimidazole Derivatives: Clean Oxidative Cleavage of 2-Mercapto Group", Organic Process Research & Development, vol. 6, pp. 674-676, 2002.
J. Hicks et al, "Synthesis of Triple (13C2, 15N), Single (14C), and Double (14C2) Labeled Trimetrexate", Journal of Labelled Compounds and Radiopharmaceuticals, vol. 29, No. 4, pp. 415-429, 1991.
J. Hynes et al, "Inhibition of Human Dihydrofolate Reductase by 2,4-Diaminoquinazolines Bearing Simple Substituents on the Aromatic Ring", J. Heterocyclic Chem., vol. 28, pp. 1981-1986, Dec. 1991.
J. Liu et al, "A Modified Procedure for the Synthesis of 1-Arylimidazoles", Synthesis, No. 17, pp. 2661-2666, 2003.
J. Scheller et al, "Interleukin-6 Trans-Signalling in Chronic Inflammation and Cancer", Scandinavian Journal of Immunology, vol. 63, pp. 321-329, 2006.
K. El-Bayouki et al, "Ethyl Chloroformate/DMF in Organic Synthesis. I. A Novel Reagent for Ring Closure of 5-Amino-1-Aryl-4-Imidazolecarboxamides to their Hypoxanthine Derivatives," Gazzetta Chimica Italiana, vol. 119, pp. 163-165, 1989.
K. Masuko-Hongo et al, "Up-Regulation of Microsomal Prostaglandin E Synthase 1 in Osteoarthritic Human Cartilage", Arthritis & Rheumatism, vol. 50, No. 9, pp. 2829-2838, Sep. 2004.
K. Matsuda et al, "One-Pot Preparation of 1-Substituted Imidazole-2-Thione from Isothiocyanate and Amino Acetal", Synthetic Communications, vol. 27, No. 20, pp. 3565-3571, 1997.
K. Walker et al, Animal models for pain research, Molecular Medicine Today, vol. 5, pp. 319-321, Jul. 1999.
L. Haywood et al, "Inflammation and Angiogenesis in Osteoarthritis", Arthritis Rheum., vol. 48, No. 8, pp. 2173-2177, Aug. 2003.
L. Liu et al, "A Soluble Base for the Copper-Catalyzed Imidazole N-Arylations with Aryl Halides", Journal of Organic Chemistry, vol. 70 (24), pp. 10135-10138, 2005.
L. Randall et al, "A Method for Measurement of Analgesic Activity on Inflamed Tissue", Arch Int. Pharmacodyn, CXL No. 4, pp. 409-419, 1957.
L. Wang et al, "Potent, Orally Active Heterocycle-Based Combretastatin A-4 Analogues: Synthesis, Structure-Activity Relationship, Pharmacokinetics, and In Vivo Antitumor Activity Evaluation", Journal of Medicinal Chemistry, vol. 45, No. 8, pp. 1697-1711, 2002.
M. Graffner-Nordberg et al, "Design, Synthesis, Computational Prediction, and Biological Evaluation of Ester Soft Drugs as Inhibitors of Dihydrofolate Reductase from *Pneumocystis carinii*", J. Med. Chem., vol. 44, (2001) pp. 2391-2402.
M. J. Benito et al, "Synovial tissue inflammation in early and late osteoarthritis", Ann Rheum Dis, vol. 64, pp. 1263-1267, 2005.
M. M. Hardy et al, "Cyclooxygenase 2-Dependent Prostaglandin E2 Modulates Cartilage Proteoglycan Degradation in Human Osteoarthritis Explants", Arthritis Rheum., vol. 46, No. 7, pp. 1789-1803, Jul. 2002.
M. Seto et al, "Orally active CCR5 antagonists as anti-HIV-1 agents. Part 3: Synthesis and biological activities of 1-benzazepine derivatives containing a sulfoxide moiety", Bioorganic & Medicinal Chemistry, vol. 13, pp. 363-386, 2005.
N. Matsunaga et al, "C17,20-Lyase Inhibitors I. Structure-based de novo design and SAR study of C17,20-lyase inhibitors", Biorganic & Medicinal Chemistry, vol. 12, pp. 2251-2273, 2004.
P. Chen et al, "Discovery and Initial SAR of Imidazoquinoxalines as Inhibitors of the Src-Family Kinase p56Lck", Bioorganic & Medicinal Chemistry Letters, vol. 12, pp. 1361-1364, 2002.
P. Erhardt et al, "Cardiotonic Agents. 5. Fragments from the Heterocycle-Phenyl-Imidazole Pharmacophore", J. Med. Chem., vol. 32, pp. 1173-1176, 1989.
P. Maligres et al, "Preparation of a Clinically Investigated Ras Farnesyl Transferase Inhibitor", J. Heterocyclic Chem., vol. 40, (2003) pp. 229-241.
R. G. Ramsay et al, "Transcriptional Regulation of Cyclo-Oxygenase Expression: Three Pillars of Control", International Journal of Immunopathology and Pharmacology, vol. 16, No. 2(S), pp. 59-67, 2003.
R. Naeini et al, "Remodelling of spinal nociceptive mechanisms in an animal model of monoarthritis", European Journal of Neuroscience, vol. 22, pp. 2005-2015, 2005.
R. Nieminen et al, "Inhibitors of Mitogen-Activated Protein Kinases downregulate COX-2 Expression in Human Chondrocytes", Mediators of Inflammation, vol. 5, pp. 249-255, 2005.
S. Mackenzie et al, "Triazines and Related Products, Part VI. Synthesis and Properties of 4-Amino-2(2H)-imino-s-triazino[1,2-c][1,2,3]-benzotriazines", J. Chem. Soc. (C), vol. 17, pp. 2298-2308, 1970.
S. Meller et al, "The Possible Role of Glia in Nociceptive Processing and Hyperalgesia in the Spinal Cord of the Rat", Neuropharmacology, vol. 33, No. 11, pp. 1471-1478, 1994.
S. U. Son et al, "Synthesis of Cu2O coated Cu nanoparticles and their successful applications to Ullmann-type animation coupling reactions of aryl chlorides", Chem. Commun., pp. 778-779, 2004.
T. Ibuki, "Cyclooxygenase-2 is induced in the endothelial cells throughout the central nervous system during carrageenan-induced hind paw inflammation; its possible role in hyperalgesia", Journal of Neurochemistry, vol. 86, pp. 318-328, 2003.
T. Uno et al, "Synthesis of Antimicrobial Agents. 1. Syntheses and Antibacterial Activities of 7-(Azole substituted) quinolones", Journal of Medicinal Chemistry, vol. 30, (1987) No. 12, pp. 2163-2169.
W. Liu et al, "Cyclooxygenase-2 is Up-Regulated by Interleukin-1B in Human Colorectal Cancer Cells via Multiple Signaling Pathways", Cancer Research, vol. 63, (2003) pp. 3632-3636.
Y. Juarranz et al, "Protective effect of vasoactive intestinal peptide on bone destruction in the collagen-induced arthritis model of rheumatoid arthritis", Arthritis Research & Therapy, vol. 7, pp. R1034-R1045, 2005.
Y. Takano et al, "Synthesis and AMPA Receptor Antagonistic Activity of a Novel Class of Quinoxalinecarboxylic Acid with a Substituted Phenyl Group at the C-7 Position", Biorganic & Medicinal Chemistry Letters, vol. 13, pp. 3521-3525, 2003.
Y. Wan et al, "Palladium-Catalyzed Amination of Aryl Bromides Using Temperature-Controlled Microwave Heating", Synthesis, No. 11, pp. 1597-1600, 2002.
Y. Wu et al, Copper-catalyzed coupling of (S)-1-(3-bromophenyl)-ethylamine and N-H containing heteroarenes using microwave heating, Tetrahedron Letters, vol. 44, pp. 4217-4218, 2003.
Z. Guan et al, "Interleukin-1B-induced Cyclooxygenase-2 Expression Requires Activation of Both c-Jun NH2-terminal Kinase and p38 MAPK Signal Pathways in Rat Renal Mesangial Cells", J. Biol. Chem., vol. 273, No. 44, pp. 28670-28676, Oct. 30, 1998.

6-1H-IMIDAZO-QUINAZOLINE AND QUINOLINES DERIVATIVES, NEW POTENT ANALGESICS AND ANTI-INFLAMMATORY AGENTS

CROSS-REFERENCE TO RELATED APPLICATIONS

This is a divisional of application Ser. No. 12/376,080 filed Feb. 2, 2009, which is the §371 national stage application of PCT International Application No. PCT/EP2006/065013 filed Aug. 3, 2006, the contents of all of which are incorporated herein by reference in their entirety.

The present invention is directed to novel 6-1H-imidazo-2-aryl and 2-heteroaryl quinazoline and quinolines, to a process for their preparation, to their pharmaceutical compositions and to the use of such compounds and their pharmaceutical compositions for the treatment of pain and inflammatory related disorders.

BACKGROUND

The conversion of arachidonic acid to prostaglandins and other eicosanoids is controlled by the two well known cyclooxygenase (COX) isoforms COX-1 and COX-2. COX-2 is an inducible isoenzyme that can be up-regulated in numerous pathologic conditions, including inflammation and cancer. Blocking COX activities with non steroidal anti-inflammatory drugs (NSAIDs) is a widely adopted clinical strategy for the treatment of inflammatory related diseases and pain. Main adverse-effects associated with the chronic usage of classical NSAIDs, are gastrointestinal serious side-effects and renal toxicity. Selective COX-2 inhibitors, though lacking for the great part the gastrointestinal toxicity typical of classical NSAIDs, have recently highlighted undesirable cardiovascular life threatening adverse-effects. An alternative to NSAIDs is the use of corticosteroids, however also in this case chronic use can result in severe side effects.

Since approaches that target gene transcription may complement or even be more successful than the enzyme inhibition, exploration of strategies to specifically block COX gene expression was the object of a remarkable scientific efforts in the last decade (R. G. Ramsay, Int. J. Immunopathol. Pharmacol., 2003, 16 (2S), 59-67). Recently, it was reported that some NSAIDs (including Celecoxib) exert part of their action directly on COX-2 transcriptional regulation, explaining why such agents display greater effects on this isoform than enzyme inhibition data would suggest (K. S. Chun, Biochem. Pharmacol. 2004, 68, 1089). Up-regulation of COX-2 is mediated by a variety of stimuli including cytokines, tumour promoters, oncogenes and growth factors. Intracellular signalling pathways which can induce and regulate COX-2 expressions are complex, and due to cell system dependence are still poorly understood. However, growing evidences suggests that IL-1β and COX-2 play a crucial role in the pathogenesis of inflammatory diseases and tumour growth. In the most of tissues, IL-1β induced COX-2 overexpression is mediated by stimulation of either protein kinase C (PKC) or Ras signal transduction system which enhances mitogen-activated protein kinase (MAPK) activity, which in turn activates transcription of COX-2 along with other cytokines. It has been recently demonstrated, in several tissues, that the three MAP kinases (p38, JNK and ERK 1/2) are involved in controlling COX-2 expression and translation. For instance, this was reported for human chondrocytes stimulated with IL-1β (N. Nieminen Mediators of inflammation, 2005, 5, 249-255), or in human colorectal cancer cells stimulated with IL-1β (W. Liu, Cancer Research, 2003, 63, 3632; Cellular Signalling, 2006, 18, 1262), and in renal mesangial cells (J. Biol. Chem. 1998, 273, 28670).

Rheumatoid arthritis (RA) is a systemic inflammatory disease characterized by articular synovitis leading to cartilage degradation and bone erosion. Rheumatoid synovium shows over expression of COX-2 which in turn give rise to massive production of $PGE_2$, responsible for vasodilatation, fluid extravasations and pain. Among a variety of mediators affecting COX-2 expression IL-1β appears to be the main triggering agent (Arthritis Research, 2005, 57).

Osteoarthritis (OA) is the most common form of arthritis, and is largely recognized to be a frequent cause of serious disability in older adults. Synovial inflammation characterized by mononuclear cell infiltration, proliferation of new blood vessels, production of pro-inflammatory cytokines and other mediators of joint damage has been highlighted in the synovial tissues from patients with early and late OA (Ann Rheum. Dis., 2005, 64, 1263-67), and the importance of synovitis in the pathophysiology of OA is increasingly recognized (Haywood, Arthritis Rheum., 2003, 48, 2173; Shibakawa, Osteoarthritis Cartilage, 2003, 11, 133). Increased expression of cytokines, COX-2, adhesion molecules and angiogenic factors are characteristics of chronic synovitis. It has been shown how $PGE_2$ produced by COX-2, in human osteoarthritis explants modulates cartilage proteoglycan degradation, thus highlighting to this inflammatory mediator not only a role in propagating the inflammation process but also a direct involvement in tissue degeneration (Arthritis Rheum., 2002, 46, 1789). It has also been demonstrated how, in OA synoviocytes the mechanism of IL-1β induction for COX-2 expressions follows the same signalling pathway above discussed for the chondrocytes (Arthritis & Rheum., 2004, 50, 2829).

Elevated levels of COX-2 expression have been detected along with high levels of IL-1β, in patients affected by inflammatory bowel disease (IBD), Crohn's disease and ulcerative colitis, where the inflammatory/autoimmune response is triggered by an exaggerated response to antigens produced by the gut bacteria.

Expression of COX-2 has been reported to be elevated in human colorectal adenocarcinoma and other tumors, including those of breast, cervical, prostate and lung. Genetic knock-out or pharmacological inhibition of both COX-2 and/ or its expression has been proven to protect against experimentally-induced carcinogenesis. Accordingly, the inhibition of abnormally or improperly elevated levels of COX-2, by blocking the enzyme and/or its expression, provides also one of the most effective and promising strategies for cancer chemoprevention.

Blockage of cytokines in inflammatory diseases, has lead to the greatest advances in medicine of recent years. Tumor necrosis factor (TNF), interleukin-1 (IL-1) and interleukin-6 (IL-6) are important biological entities collectively referred to as pro-inflammatory cytokines, which play a role in several diseases, for example such as toxic shock syndrome, RA, OA, diabetes and IBD. In these diseases, chronic elevation of inflammation exacerbates or causes much of the observed pathophysiology. Pro-inflammatory cytokines play a decisive role in the generation of the inflammatory and destructive cartilage degeneration as well as bone erosion in arthritis (B. Moller, Springer Semin. Immunopathol., 2006, 391). Due to resulting structural damage, bone erosion is a major reason for disability in arthritis patients. Bone erosion in arthritis is a consequence of synovial osteoclast formation (B F. Boyce, Curr. Opinion Rheumatol, 2006, 18, 427). Inflammatory cytokines produced in inflamed synovium induce in the bone marrow the release of osteoclast precursors, which reached the inflamed joints and in response to cytokine stimuli differentiate into the bone-resorbing osteoclasts. Thus, pro-inflammatory cytokines in arthritis are responsible for both the progression and diffusion of the inflammatory status within the joint as well as the bone damage. Antagonists of IL-1β have been shown to reduce the degradation of cartilage matrix components in a variety of experimental models of arthritis. Interleukin-6 (IL-6) is a pro-inflammatory cytokine, prevalently expressed in activated monocytes and macrophages, which plays a fundamental role in many chronic inflammatory diseases, particularly implicated in the acute phase response and critically involved in the maintenance of the disease state (J. Scheller, Scand. J. Immunol., 2006, 63, 321). Overexpression of IL-6 has been implicated in the pathology of IBD, arthritis (RA and OA), asthma, colon cancer, multiple myeloma, post-menopausal osteoporosis.

A number of anti-cytokines therapies are currently in clinical trials, and several monoclonal antibodies against TNF and recombinant soluble TNF receptor (Etanercept, Enbrel) as well as recombinant soluble IL-1 receptor (Anakinra, Kineret) reached the market, demonstrating a pronounced activity in treating diseases such as RA, IBD and Crohn's disease. These biological high-molecular weight products, which are based on the antagonism of the circulating cytokine, are however expensive, limited to parenteral administration route and can give rise to immunogenic adverse effects, likely due to their biological nature.

Strategies aimed at blocking cytokine production with small molecules are still of great therapeutic interest, since could be more efficient in blocking cytokine circulation, not endowed with the immunogenic adverse effect of the biological product, less expensive and of simpler administration route. In addition, simultaneous blockade of COX-2 production and pro-inflammatory cytokines production should interrupt the self propagating loop which has been found relevant for the triggering and maintenance of the pathology in inflammatory diseases.

As discussed above, inflammation causes the induction of COX-2, leading to the release of prostanoids, which sensitize peripheral nociceptor terminals and produce localized pain hypersensitivity, however peripheral inflammation also generates central sensitization by direct widespread induction of COX-2 expression in spinal cord and CNS neurons, which results in an increased neuronal excitability and pain hypersensitivity (J. Neurochem., 2003, 86, 318).

Although arthritis (OA and RA) is defined as inflammation of the joints, the primary feature with which patients present in the clinic is chronic pain; even though arthritis is not the only pathology which can give rise to chronic pain, it is rather common and quite representative of this kind of pain. Chronic pain can be divided into inflammatory pain, a kind of pain more related to peripheral tissue damage/inflammation, and neuropathic pain. Neuropathic pain refers clinically to a group of chronic pain syndromes. These syndromes share the common feature that they are caused by an initial nerve damage, which subsequently results in an abnormal sensory processing in the central and peripheral nervous system. Neuropathic pain conditions are the consequence of a number of diseases, for instance diabetes, cancer, amputees, multiple sclerosis.

Peripheral sensitization and central sensitization are the two major mechanisms underlying the generation of pain. When tissue damage occurs, mechanisms in both the nervous and the immune system trigger the release of sensitizing agents such as pro-inflammatory prostaglandins (PGE$_2$), 5-HT, bradykinin, histamine, ATP, cytokines from inflammatory cells and nerve terminals. These mediators evoke activation of specific ion channels through the excitation of peripheral nociceptive neurons, involving activation of intracellular kinases, and resulting in peripheral sensitization. Activation of peripheral nociceptors also reflects in a dependent neuronal plasticity in the CNS. This plasticity modifies the performance of nociceptive pathway by enhancing and prolonging the responses to subsequent peripheral stimuli. These changes in the spinal cord, as well as in the brain are referred to central sensitization. Central sensitization plays a major role in maintaining elevated pain sensitivity and it is responsible for the pain produced after injury by normally innocuous low threshold afferent inputs. A so complex mechanism for pain induction and control can explain why the treatment of pain conditions has not found yet a satisfactory pharmacological solution.

In order to identify effective agents for the clinical management of pain, several alternate pharmacological approaches have been carried out in the last decade, for example COX-2 inhibitors, displayed a good efficacy in the treatment of inflammatory pain, but lacked effectiveness in the treatment of neuropathic pain, in addition for COX-2 inhibitors the undesirable life threatening side-effects mentioned above suggest not to use these drugs for clinical management of chronic pain. The available analgesics for the treatment of neuropathic pain, for instance some tricyclic antidepressant (e.g.: Amitriptyline) and a few antiepileptic drugs (e.g. gabapentin, lamotrigine, and carabamazepine) are effective in some patients, however there is still a large need for efficient drugs for neuropathic pain treatment.

Pharmacological agents acting at controlling cytokines and PGE$_2$ expression can counteract the above described mechanisms of peripheral and central sensitization thus acting as efficient and potent analgesics (M. Schafer, Immune Mechanisms of Pain and Analgesia, pg. 41-50 Plenum Publishers, 2003).

DESCRIPTION OF THE INVENTION

The present invention comprises a new class of compounds, 6-1H-imidazole derivatives of 2-aryl and heteroaryl quinazolines and quinolines of Formula (I), useful for the pharmacological treatment of inflammatory diseases such as arthritis, typically rheumatoid arthritis and osteoarthritis, asthma and inflammatory diseases of the respiratory tract, chronic obstructive pulmonary disease (COPD), systemic lupus erythematosus, skin diseases such as eczema, psoriasis and dermatitis, gastrointestinal serious inflammatory conditions such as inflammatory bowel disease (IBD), ulcerative colitis, Crohn's disease (CD), post operative inflammatory complications, and cancer including but not limited to: colon cancer, multiple myeloma, breast, cervical, prostate and lung cancer. In addition compounds of the invention act as potent analgesics, independently upon the pain was inflammatory pain or neuropathic pain. Accordingly, the compounds of the invention are useful for the treatment of both acute and chronic pain, including but not limited to: postoperative pain, muscular pain, pain resulting from various forms of trauma, as well as chronic pain, neuropathic pain, cancer pain, pain caused by arthritis and visceral pain.

Compounds of Formula (I):

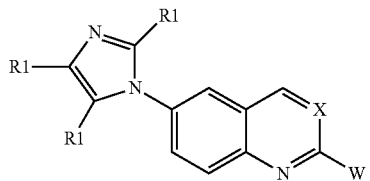

wherein:
- X is independently selected from a carbon or a nitrogen atom;
- W is independently selected from an aryl group or an hetheroaryl group of Formula II:

Group of Formula II:

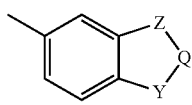

when W is an aryl group, it is intended an unsubstituted or substituted phenyl, with one or more substituents independently selected from halogen (—F, —Cl, —Br), trifluoromethyl (—CF$_3$), alkyl (—R$_2$), hydroxyl (—OH), alkoxy (—OR$_2$), trifluoromethoxy (—OCF$_2$), cyano (—CN), carboxamido (—CONHR$_3$ or —NHCOR$_3$ or —CONR$_2$R$_3$ or —NHCOR$_3$), carbonyl (—CO—R$_3$), alkylthio (—SR$_2$), sulfinyl (—SOR$_3$) and sulfonyl (—SO$_2$R$_2$);

when W is an heteroaryl group of Formula II, it is a benzocondensed-5 or -6 membered heterocycle, wherein:
- Z and Y are independently selected from: an oxygen atom (—O—), a sulphur atom (—S—), or the groups: —SO$_2$—, —CHR$_3$—, —CR$_3$=, —NH—, —N=;
- Q is independently selected from the groups: —CHR$_3$—, —CH=, —CR$_3$=, —CHR$_3$—CH$_2$—;

provided that the combination of Y, Z, Q groups give rise to: 1,3-benzodioxole, 1,3-benzodithiol, benzofuran, 2,3-dihydrobenzofuran, benzothiophene, 2,3-dihydrobenzothiophene, 2,3-dihydrobenzothiophene S,S-dioxide, indole, 2,3-dihydroindole, benzimidazole, benzoxazole, benzothiazole, 2H-3,4-dihydrobenzopyran, 2H-3,4-dihydrobenzothiopyran, 2H-3,4-dihydrobenzothiopyran S,S-dioxide, [1,4]-benzodioxine, 2,3-dihydro-[1,4]-benzodioxine (1,4-benzodioxan), 1,4-benzothiazine, 2,3-dihydro-[1,4]-benzothiazine, 2,3-dihydro-[1,4]-benzothiazine S,S-dioxide, [1,4]-benzoxazine, 2,3-dihydro-[1,4]-benzoxazine;

- R$_1$ is independently selected from hydrogen (—H) or C$_1$-C$_4$ alkyl or hydroxymethyl (—CH$_2$OH), aminomethyl (—CH$_2$NH$_2$), dimethylaminomethyl (—CH$_2$NMe$_2$), trifluoromethyl (—CF$_3$); the C$_1$-C$_4$ alkyl group is a linear or branched hydrocarbon chain; provided that in compounds of formula I not more than two R1 groups are simultaneously C$_1$-C$_4$ alkyl or trifluoromethyl (—CF$_3$) and only one R1 group is hydroxymethyl (—CH$_2$OH), aminomethyl (—CH$_2$NH$_2$) or dimethylaminomethyl (—CH$_2$NMe$_2$);
- R$_2$ is independently selected from C$_1$-C$_6$ alkyl or aryl; for C$_1$-C$_6$ alkyl herein is intended a linear or branched, saturated or unsaturated C$_1$-C$_6$ hydrocarbon chain optionally substituted with an aryl, aryl being herein intended as defined above;
- R$_3$ is independently selected from hydrogen, C$_1$-C$_6$ alkyl and aryl. For C$_1$-C$_6$ alkyl herein is intended a linear or branched, saturated or unsaturated C$_1$-C$_6$ hydrocarbon chain optionally substituted with an aryl, aryl being herein intended as defined above.

According to this invention the compounds of Formula (I) may be used as the free base or as a pharmaceutically acceptable salt thereof, or as a solvate or hydrate form of such salt.

The salts of the compounds of Formula (I) are pharmaceutically acceptable addition salts with inorganic and organic acids. Representative not limiting examples of inorganic salts are: hydrochloride, hydrobromide, hydrogensulphate and sulphate. Representative not limiting examples of organic salts are: maleate, fumarate, oxalate, methanesulfonate, succinate, ascorbate, tartrate.

In another embodiment this invention provides methods for the preparation of compounds of Formula (I).

In a further embodiment this invention provides pharmaceutical compositions for compounds of Formula (I), useful for the treatment of pain and inflammatory disorders as discussed above. Within the scope of the present invention the term pharmaceutical composition (drug product) refers to any oral, parenteral or topical dosage form, suitable for the treatment of the above pathologies, that contains an effective amount of at least one of the active pharmaceutical ingredients (drug substances), compounds of Formula (I), its salts or solvates thereof, and a pharmaceutically acceptable carrier, excipients or diluents as defined below, for oral, parenteral or topic administration.

Representative not limiting examples of compounds of Formula (I) are listed in Table 1.

TABLE 1

| Name | Structure | MW | Example |
|---|---|---|---|
| [2-phenyl-6-(1H-imidazol-1-yl)]quinazoline | 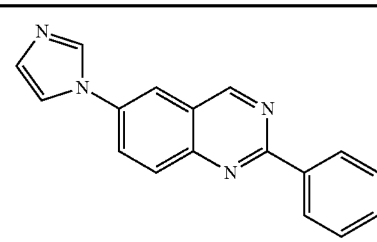 | 272.31 | 1 |

TABLE 1-continued

| Name | Structure | MW | Example |
|---|---|---|---|
| [2-phenyl-6-(1H-imidazol-1-yl)]quinoline | 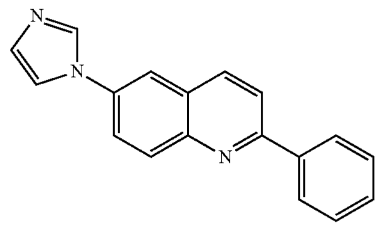 | 271.32 | 2 |
| [2-(1,3-benzodioxol-5-yl)-6-(1H-imidazol-1-yl)]quinazoline | 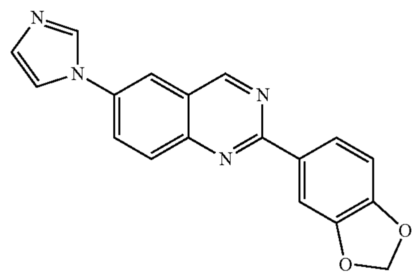 | 316.32 | 3 |
| [2-(benzofuran-5-yl)-6-(1H-imidazol-1-yl)]quinazoline dihydrochloiride | 2·HCl | 385.25 | 4 |
| [2-(2,3-dihydro-1,4-benzodioxin-6-yl)-6-(1H-imidazol-1-yl)quinazoline | 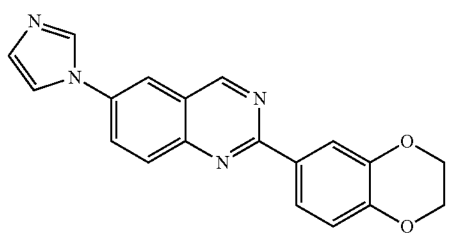 | 330.35 | 5 |
| [2-(3,4-dichlorophenyl)-6-(1H-imidazol-1-yl)]quinazoline | 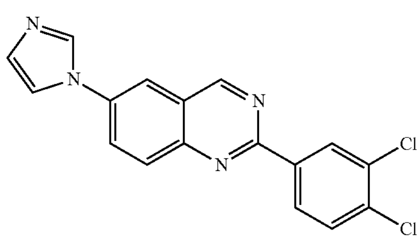 | 341.20 | 6 |
| [2-[(4-benzyloxy)phenyl-6-(1H-imidazol-1-yl)]quinazoline dihydrochloride | ·2HCl | 451.36 | 7 |

TABLE 1-continued

| Name | Structure | MW | Example |
|---|---|---|---|
| [2-(4-chlorophenyl)-6-(1H-imidazol-1-yl)]quinazoline | 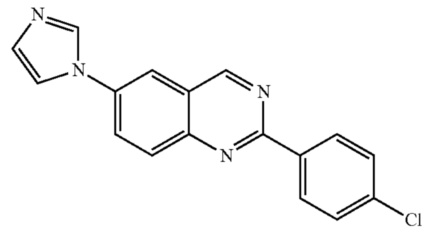 | 306.76 | — |
| [2-(4-fluorophenyl)-6-(1H-imidazol-1-yl)]quinazoline | 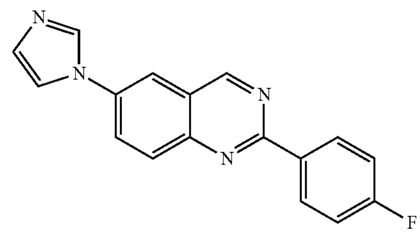 | 290.30 | — |
| [2-(3,4-difluorophenyl)-6-(1H-imidazol-1-yl)]quinazoline | 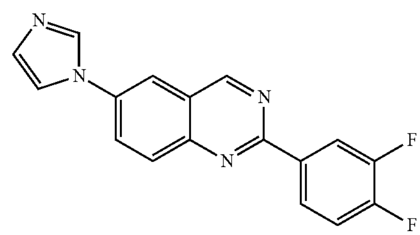 | 308.29 | — |
| [2-(4-methoxyphenyl)-6-(1H-imidazol-1-yl)]quinazoline | 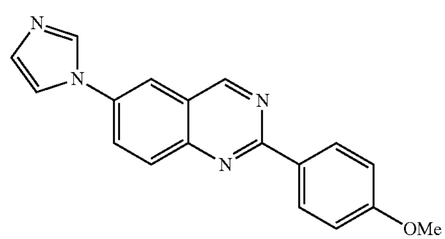 | 302.34 | — |
| [2-(2,3-dihydro-benzofuran-5-yl)-6-(1H-imidazol-1-yl)]quinazoline | 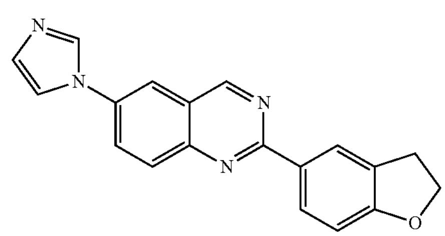 | 314.35 | — |
| [2-(benzoxazol-5-yl)-6-(1H-imidazol-1-yl)]quinazoline | 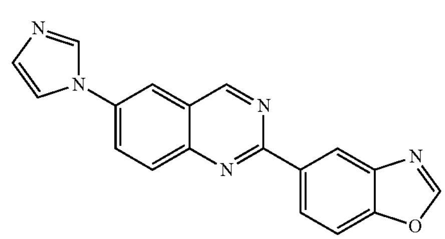 | 313.32 | — |

TABLE 1-continued

| Name | Structure | MW | Example |
|---|---|---|---|
| [2-(2H-3,4-dihydro-1-benzopyran-6-yl)-6-(1H-imidazol-1-yl)]quinazoline | 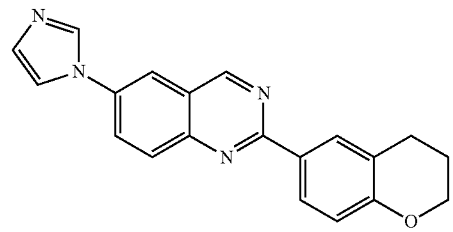 | 328.38 | — |
| N-[2-(2,4-dihydro-benzothiophen-1,1-dioxide-5-yl)-6-(1H-imidazol-1-yl)]quinazoline | 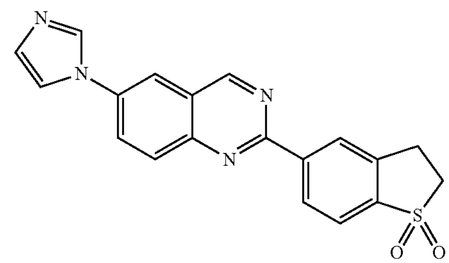 | 362.41 | — |
| [2-(4-fluorophenyl)-6-(1H-imidazol-1-yl)]quinoline | 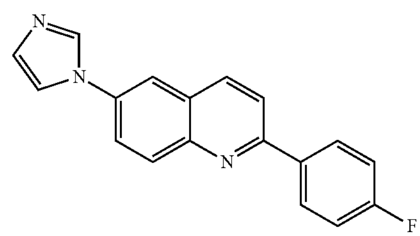 | 289.31 | — |
| [2-(3,4-difluorophenyl)-6-(1H-imidazol-1-yl)]quinoline | 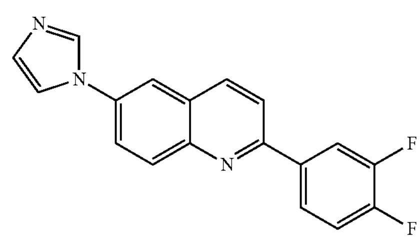 | 307.31 | — |
| [2-(4-methoxyphenyl)-6-(1H-imidazol-1-yl)]quinoline | 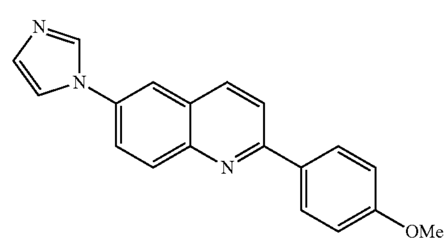 | 302.34 | — |
| [2-(2,3-benzodioxol-5-yl)-6-(1H-imidazol-1-yl)]quinoline | 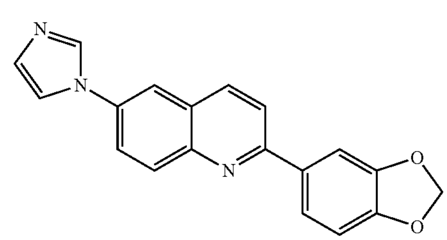 | 315.33 | — |

TABLE 1-continued

| Name | Structure | MW | Example |
|---|---|---|---|
| [2-(benzoxazol-5-yl)-6-(1H-imidazol-1-yl)]quinoline | 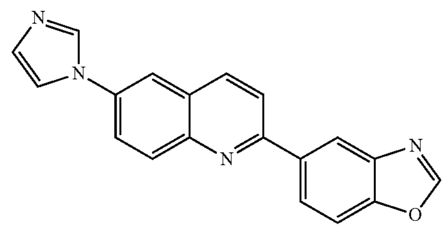 | 312.33 | — |
| [2-(2,3-dihydro-benzofuran-5-yl)-6-(1H-imidazol-1-yl)]quinoline | 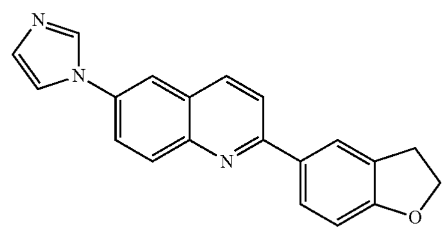 | 316.36 | — |
| [2-(benzofuran-5-yl)-6-(1H-imidazol-1-yl)]quinoline | 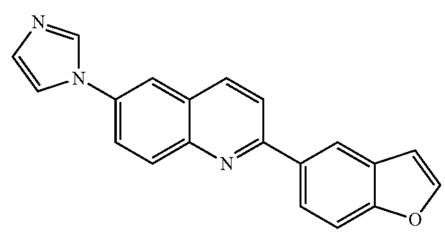 | 311.35 | — |
| [2-(2H-3,4-dihydro-1-benzopyran-6-yl)-6-(1H-imidazol-1-yl)]quinoline | 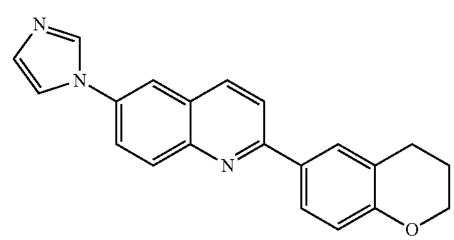 | 327.39 | — |
| [2-[(4-benzyloxy)phenyl-6-(1H-imidazol-1-yl)]]quinoline | 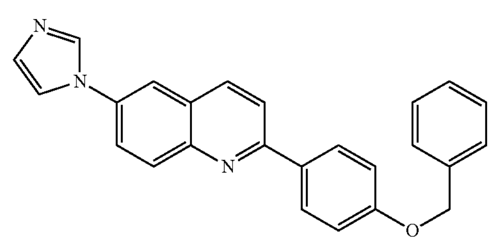 | 377.45 | — |
| [2-[(4-phenyloxy)phenyl-6-(1H-imidazol-1-yl)]]quinoline | 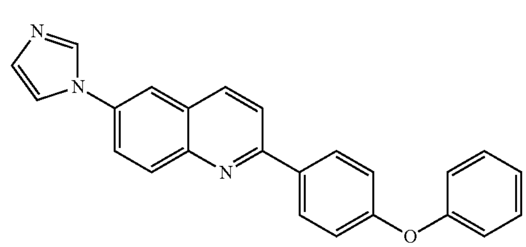 | 363.42 | — |

TABLE 1-continued

| Name | Structure | MW | Example |
|---|---|---|---|
| [2-[(4-fluorophenyloxy)phenyl-6-(1H-imidazol-1-yl)]]quinoline | 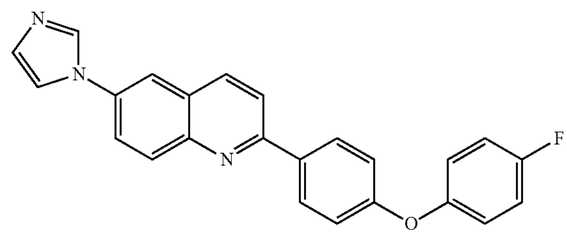 | 381.41 | — |
| [2-[(4-fluorophenyloxy)phenyl-6-(2-methyl-1H-imidazol-1-yl)]]quinoline | 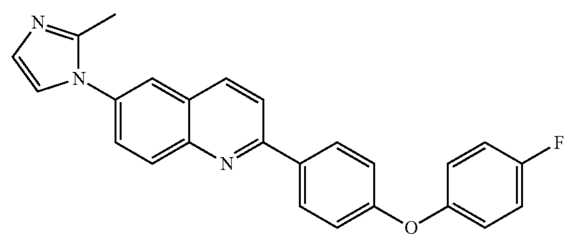 | 395.44 | — |
| [2-(1,3-benzodioxol-5-yl)-6-(2-methyl-1H-imidazol-1-yl)]quinazoline | 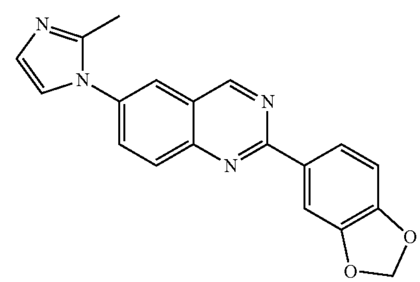 | 330.35 | — |
| [2-(1,3-benzodioxol-5-yl)-6-(4-methyl-1H-imidazol-1-yl)]quinazoline | 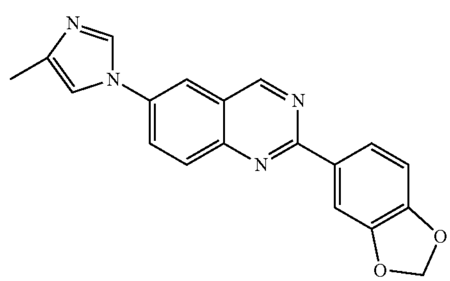 | 330.35 | — |
| [2-(1,3-benzodioxol-5-yl)-6-(4-methyl-1H-imidazol-1-yl)]quinoline | 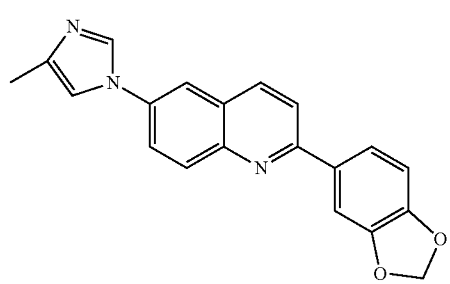 | 329.36 | — |

Preparation of the Compounds of the Invention

Compounds of Formula (I) can be prepared by reacting a compound of Formula III with an imidazole derivative of Formula (IV) as depicted in Scheme 1, wherein X, W and $R_1$ have the same meanings as discussed above for compounds of Formula (I) and Hal is an halogen atom such as fluorine, chlorine, bromine and iodine, typically bromine and iodine.

Scheme 1:

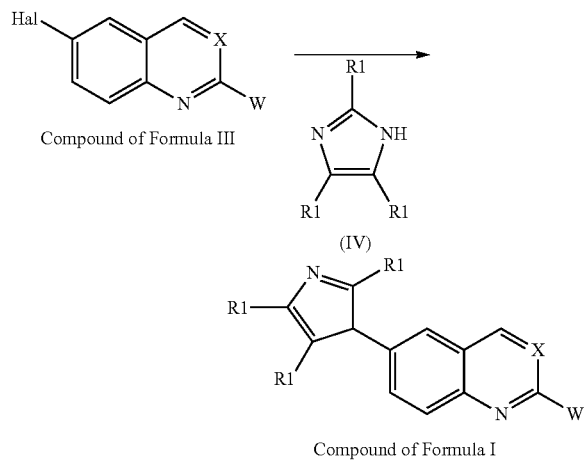

The reaction of a compound of Formula III can be carried out using an imidazole derivative of Formula IV as free base or its alkaline metal salt (sodium, lithium or potassium salt), in the presence of a suitable catalyst, in a solvent such as dimethylformamide (DMF), dimethylsulfoxide (DMSO), acetonitrile, N-methylpyrrolidone (NMP), dimethoxyethane, tetrahydrofurane (THF), toluene or xylene, at a temperature ranging from 50° C. to 200° C.

Reaction of imidazole derivatives of formula IV with aryl halides of formula III can be carried out for example, in the presence of copper catalyst (CuI), using potassium carbonate or cesium carbonate as base, in DMF at 100° C., as reported for other substrates (J. Med. Chem., 2002, 45, 1697-1711). Alternatively, a mixture of Cu/CuO can be used as catalyst, in a DMSO-toluene mixture (Chem. Comm., 2004, 7, 778-779). Reaction of imidazole derivatives of formula IV, wherein R1 in position 2 is alkyl, with aryl halides of formula III can be carried out using triethylammonium carbonate as base, CuI as catalyst, 8-hydroxyquinoline as ligand in a mixture DMF-water as solvent, as reported for other substrates (J. Org. Chem., 2005, 70, 10135). Compounds of formula I, wherein R1 in position 4 is alkyl or hydroxymethyl, can be easily obtained by reacting compounds of formula IV, wherein R1 in position 5 is alkyl or hydroxymethyl, with the halide of formula IV using CuI as catalyst, $Cs_2CO_3$ as base and DMF as solvent as reported for other substrates (J. Org. Chem. 2004, 69, 5578; Bioorg. Med. Chem. Lett., 2003, 13, 3521). Compounds of formula I, wherein R1 in position 4 is aminomethyl or dimethylaminomethyl can be easily obtained using procedures similar to the ones described for other substrates (J. Med. Chem., 1987, 12, 2163-9; Synthesis, 1983, 1, 47-9).

Reaction of imidazole derivatives of formula IV with aryl halides of formula III can be carried out also using copper catalyst and the sodium salt of the derivative of formula IV, analogously to the literature (Bioorg. Med. Chem., 2004, 12, 2251). The compounds of formula IV as sodium salt are reacted with the aryl halide, in the presence of catalytic amounts of CuO, in DMF at 150° C. Alternatively, aryl bromides can be transformed into the corresponding N-imidazolyl derivatives by treating them with two equivalents of imidazole (as free base) in the presence of copper bromide or iodide (10% mol) and potassium carbonate in NMP, under microwave irradiation (Terahedron Lett., 2003, 4217-4218). Buchwald et al. demonstrated that the N-arylation of imidazoles can be accomplished in high yields and avoiding too drastic conditions, using $Cu(OTf)_2$.benzene complex as copper source and cesium carbonate as base, in the presence of 1,10-phenantroline and dba (dibenzylidene acetone) as additives, in xylene at 110-125° C. (Tetrahedron Lett., 1999, 40, 2657); this methodology can be successfully applied for converting compounds of formula III into compounds of formula I. Catalyzed addition of imidazole derivatives of Formula IV to aryl halides of formula III can be also carried out using Palladium as catalyst, alone or in combination with copper. The methodology of Buchwald-Hartwig for imidazole addition to aryl bromides, in DMF as solvent, using both Binap [2,2'-bis(diphenylphosphino)-1,1'-binaphtyl] or Dppf [1,3-bis(diphenylphosphino propane]palladium soluble catalysts, and potassium tert-butylate as base under microwave heating (Y. Wan, Synthesis 2002, 11, 1597-1600), can be successfully extended to the preparation of compounds of formula I starting from halides of formula III. Compounds of formula I where at least one of R1 substituents is a trifluoromethyl group can be prepared by N-arylation using analogue procedures (J. Med. Chem., 1989, 32, 575).

Alternatively, a compound of Formula I can be prepared from a compound of Formula V by reaction with glyoxal or a dicarbonyl derivative of formula VI in the presence of formaldehyde or of an aldehyde of formula $R_1CHO$ and ammonium chloride, as depicted in Scheme 2.

Scheme 2:

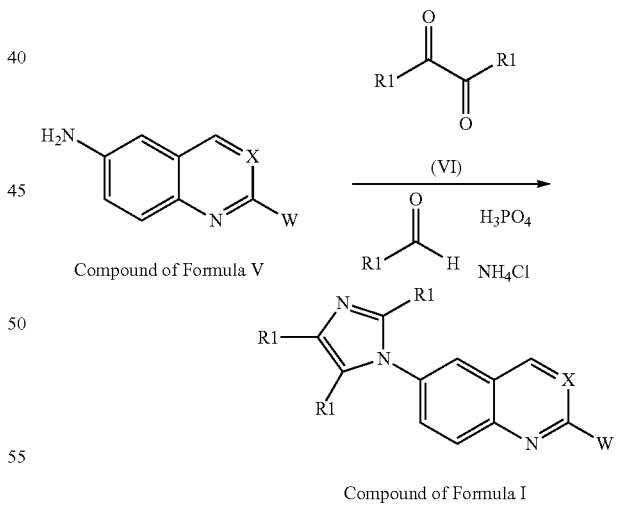

Wherein X, W and $R_1$ have the same meanings as discussed for compounds of Formula (I).

The reaction is usually carried out in methanol or ethanol in the presence of a suitable acid catalyst such as phosphoric acid. Compounds of Formula I, where all R1 are hydrogen atoms, can be obtained in satisfactory yields by treating compounds of formula V with glyoxal, in methanol, typically at room temperature, then adding $NH_4Cl$ and formaldehyde, and heating at reflux, finally phosphoric acid is added. Compounds of Formula I bearing substituted imidazoles can be prepared by the same procedure, but using a dicarbonyl compound of formula VI (wherein at least one R1 is not hydrogen) as described for other substrates (Synthesis, 2003, 2661-2666). Optionally, an aldehyde of formula $R_1CHO$ can be used instead of formaldehyde.

Alternatively, a compound of Formula I, where R1 at position 2 and 5 is hydrogen, can be prepared from a compound of Formula V by reaction with thiophosgene, followed by addition and cyclization of the amine of formula (VII), the resulting imidazol-2-thione is then desulfurized to the corresponding compound of Formula I as summarized in Scheme 3.

Scheme 3:

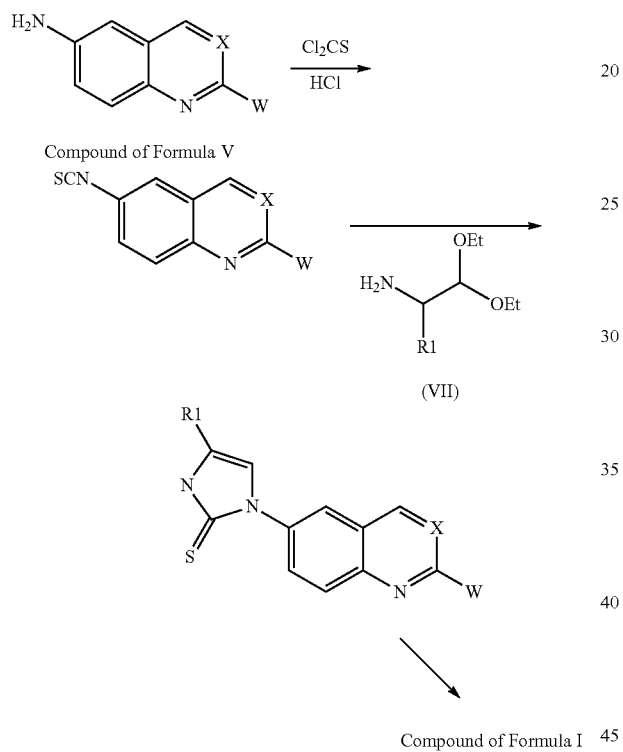

Compound of Formula I

Wherein X, W and $R_1$ have the same meanings as reported for compounds of Formula (I). The reaction involves the formation of a thiocyanate adding thiophosgene to an aqueous hydrochloric acid solution of the compound of formula V. The resulting isothiocyanate is reacted with aminoacetaldehyde dialkyl acetal (usually dimethyl or diethyl acetal) in alcohol as solvent, at the reflux temperature and in the presence of an organic base. The resulting quinoline or quinazoline imidazol-2-thione derivative is treated with 20% nitric acid and heated at about 100° C. to provide compounds of Formula I. A milder procedure, involving the use of diluted nitric acid and sodium nitrite at temperatures not exceeding 0° C., can be used for sensible compounds, according to Bioorg. & Med. Chem., 2004, 13, 363-386. Moreover, acid sensible 2-thioimidazolyl-substituted quinoline or quinazoline derivatives can be desulfurized to compounds of Formula I using nickel raney in alcoholic solvents such as ethanol or methanol (Archin. Der Pharmazie, 2002, 335, 69-76), or $H_2O_2$ in acetic acid (J. Het. Chem., 2003, 40, 229), or using $H_2O_2$ in the presence of a transition metal catalyst (Org. Process Res. & Dev., 2002, 674). Some variations in the preparation of the 2-thioimidazolyl-substituted quinoline or quinazoline derivatives, applicable to the preparation of the several compounds of Formula I can be carried out according to procedures reported in the literature for other substrates (Synthetic Commun. 1997, 27, 3565; Synthesis, 1987, 12, 1136; Synthesis 1978, 10, 741).

Alternatively, a compound of Formula I where X is a carbon atom, can be prepared from a compound of Formula VIII by reaction with a boronate of formula IX or IXa (scheme 4).

Scheme 4:

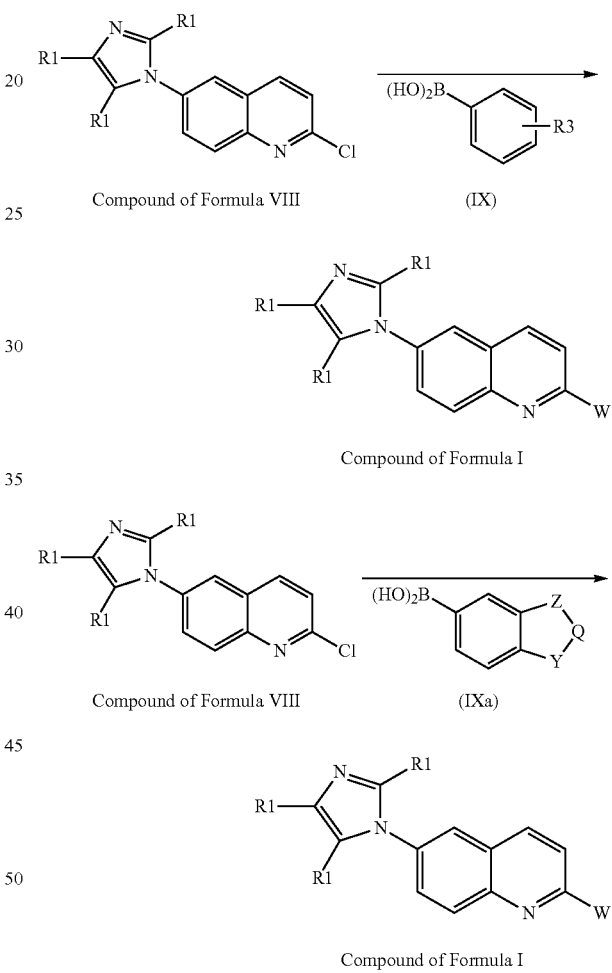

Compounds of Formula VIII can be prepared, according to Scheme 5, from a carbostiryl derivative of formula VIIIa. The carbostiryl derivative of formula VIIIa being prepared according to known methods from 6-bromo-carbostiryl (Walker et al., U.S. Pat. No. 4,792,561, Dec. 20, 1988). Appropriate reaction conditions for transforming VIIIa into VIII are as described (Biochemistry, 2005, 44, 9637; Bioorg. Med. Chem. Lett., 2002, 12, 1361; Gazzetta Chimica It., 1989, 119, 163). Compounds of formula IX and IXa are commercial compounds or can be prepared from commercial compounds according to standard procedures.

Scheme 5:

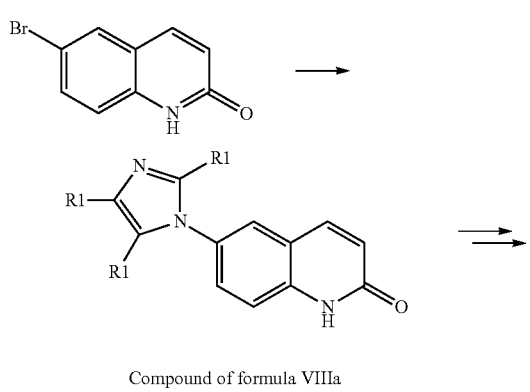

Compound of formula VIIIa

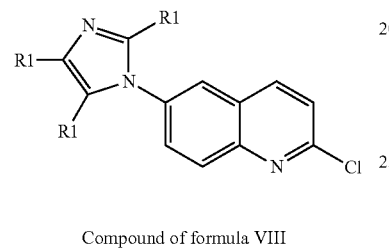

Compound of formula VIII

Compound of Formula III where the halogen atom is bromine can be obtained from compound of Formula V by diazotization in the presence of HBr and CuBr, according to known methods (J. of Labelled Compounds, 1991, 29, 415), as depicted in Scheme 6, wherein X and W have the same meanings as discussed above for compounds of Formula (I). Aryl iodides can be obtained by reaction of a compound of formula V with $NaNO_2$ and HCl in the presence of KI (J. Med. Chem., 2001, 15, 2391). Aryl chlorides can be obtained by diazotization in the presence of CuCl (J. Het. Chem. 1991, 28, 1981). Compound of formula VIIIa can be obtained from 6-bromocarbostiryl using analogue procedures as those described for Scheme 1 (J. Med. Chem., 1989, 32, 1173).

Scheme 6:

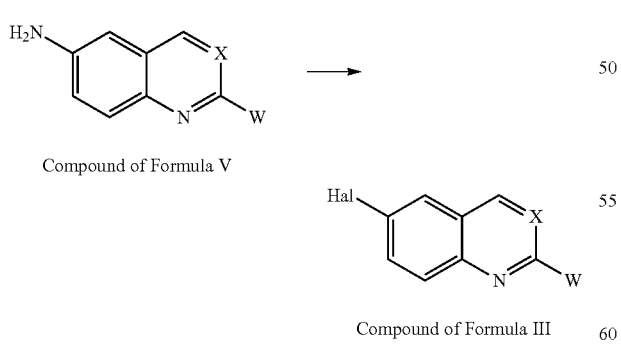

Alternatively, when in compounds of Formula I X is nitrogen, compounds of formula III can be obtained by reaction of acyl chlorides of formula X or Xa with benzylamine derivatives of formula XI, followed by cyclization and aromatization as summarized in Scheme 7.

Scheme 7:

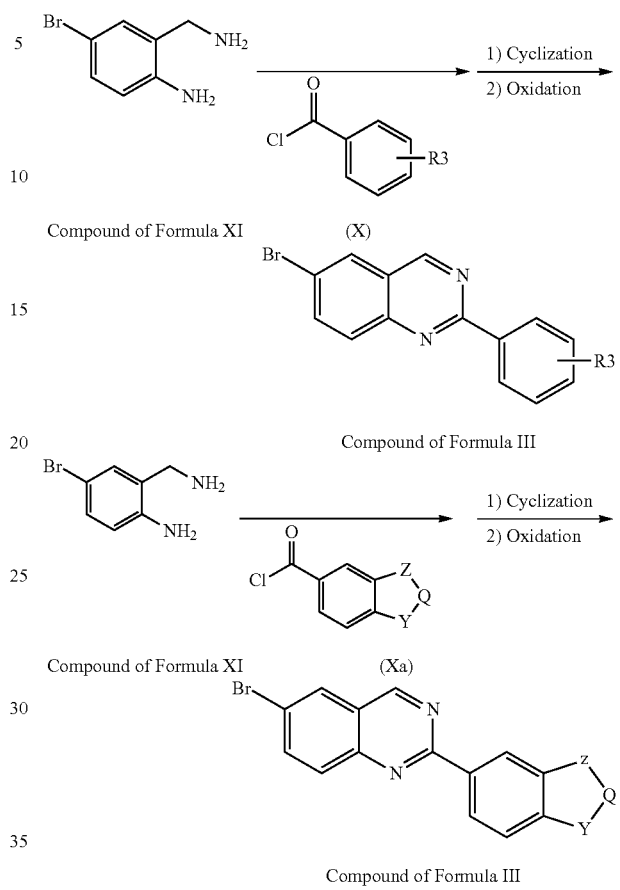

Wherein $R_3$, Y, Z, and Q have the same meanings as for compounds of Formula (I). Compounds of formula XI are prepared according to know methods.

Not limiting representative examples for preparations of compounds of Formula (I) are reported below.

Example 1

[2-phenyl-6-(1H-imidazol-1-yl)]quinazoline

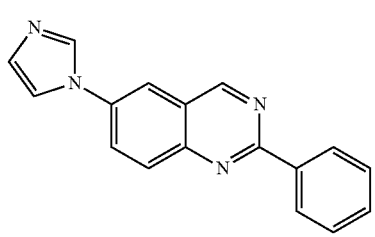

To a solution of imidazole (1.53 g, 2.24 mmol) in DMF (3 ml), under $N_2$, was added NaH (60% dispersion in oil, 0.85 g, 2.2 mmol) portion wise, the mixture was stirred for 10 min at r.t. Then 6-bromo-2-phenyl-quinazoline (2.0 g, 0.7 mmol) and CuO (0.19 g, 0.24 mmol) were added, the mixture was heated at 150° C. for 6 h, cooled and poured onto water. The precipitate was filtered, washed with water and dissolved in hot AcOEt/THF 1/1. The insoluble material was filtered off and the filtrate was concentrated. The obtained solid was triturated with diisopropyl ether and dried in vacuum (1.08 g, 57% yield). $C_{17}H_{12}N_4$; MW: 272.31; mp 153.8-158.7° C.; $^1$H NMR (DMSO-d6) 9.72 (s, 1H), 8.39-8.63 (m, 5H), 8.23 (d, 1H), 8.00 (s, 1H), 7.58-7.62 (m, 3H), 7.23 (s, 1H); IR (KBr) 1556, 1506, 1379; TLC (CHCl$_3$:MeOH 9:1) Rf=0.50

6-bromo-2-phenyl-quinazoline

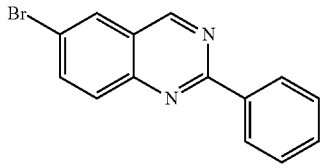

To a suspension of 5-bromo-2-amino-benzylamine dihydrochloride (38 g, 0.138 mol) in dichloromethane (DCM) (1 l) was added at 0° C. triethylamine (TEA) (67.5 ml, 0.485 mol) and a solution of benzoyl chloride (17 ml, 0.145 mol) in DCM (200 ml). The mixture was stirred for 1 h at r.t. Water was added and the organic phase was separated, washed with water and dried over Na$_2$SO$_4$. The solvent was removed in vacuum (i.v.) and the residue suspended in POCl$_3$ (200 ml). The mixture was heated at reflux for 1 hour, then the solvent was removed i.v., and the residue partitioned between AcOEt and 0.1 N NaOH. The organic layer was washed with 0.1 N NaOH and water, then dried over Na$_2$SO$_4$ and concentrated i.v. to provide a solid. A mixture of the obtained solid and chloranil (35 g, 0.138 mol) in toluene (600 ml) was heated at reflux for 4 hours. The mixture was concentrated i.v. and the residue was treated with DCM. The insoluble was filtered off and washed with DCM. The combined filtrates were washed with 0.1 N NaOH and then with water. The solution was dried over Na$_2$SO$_4$ and concentrated i.v. The obtained solid was triturated with methanol and dried i.v. (22 g, 56% yield). $C_{14}H_9BrN_2$; MW: 285.15; $^1$H NMR (DMSO-d6) 9.70 (s, 1H), 8.49-8.56 (m, 3H), 8.17 (dd, 1H), 8.02 (d, 1H), 7.58-7.61 (m, 3H); TLC (AcOEt:PE 2:8) Rf=0.70.

5-bromo-2-amino-benzylamine dihydrochloride

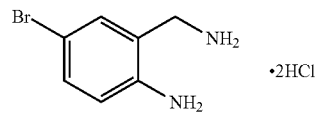

A solution of borane in THF (1 M, 400 ml) was added at 0° C. to a suspension of 5-bromo-anthranilonitrile (60 g, 0.304 mol, prepared as described in S. M. Mackenzie et al, *J. Chem. Soc. C,* 1970, 17, 2298-2308) in THF (450 L), under N$_2$. The mixture was stirred for 72 hours at r.t. After cooling at 0° C. absolute EtOH was added, then HCl was bubbled through the solution. The mixture was concentrated i.v. pressure and the residue was triturated with diisopropyl ether. The obtained solid was dried i.v. to give the titled product (76.6 g, 91.4% yield). $C_7H_9BrN_2$. 2HCl, MW 273.9; $^1$H NMR (DMSO-d6) 8.57 (s, 2H), 7.73 (s, 1H), 7.55 (dd, 1H), 7.24 (d, 1H), 5.82 (s, 4H), 4.13 (s, 2H); TLC (CHCl$_3$:MeOH:H$_2$O:NH$_3$ 85:25:2:1) Rf=0.3.

Example 2

[2-phenyl-6-(1H-imidazol-1-yl)]quinoline

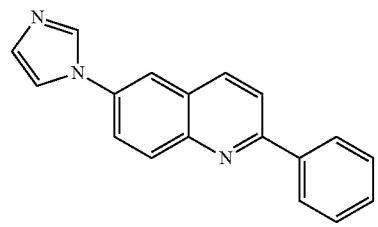

2-phenyl-6-amino-quinoline (1.0 g, 4.54 mmol) (prepared as described in EP1571142) dissolved in methanol (20 ml) was treated with 40% aq glyoxal (0.52 ml, 4.54 mmol) for 20 hours at r.t. NH$_4$Cl (486 mg, 9.08 mmol) was added followed by 37% aq. formaldehyde (0.68 ml, 9.08 mmol). The mixture was diluted with methanol (200 ml) and refluxed for 1 hour. H$_3$PO$_4$ (0.64 ml, 85%) was added over 10 minutes. The resulting mixture was then stirred at reflux for a further 20 hours. After removal of the solvent, the dark residue was poured onto ice and neutralized with aq 30% NaOH until pH 9. The resulting mixture was extracted with Et$_2$O. The organic phases were combined and washed with water, brine and dried (Na$_2$SO$_4$). The solvent was removed and the residue was triturated with isopropyl ether to afford 700 mg (yield: 57%) of the titled product. $C_{18}H_{13}N_3$, M.W. 271.32. mp: 141.7-147.5° C., $^1$H-NMR (d$_6$-DMSO): 8.52 (d, 1H); 8.30-7.92 (m, 6H); 7.60-7.25 (m, 5H); 7.20 (s, 1H). MS: M$^+$ 272; IR(KBr): 3391, 3055, 1620, 1598, 1499 cm$^{-1}$. TLC: (9/1 chloroform/methanol) Rf=0.50.

Example 3

[2-(1,3-benzodioxol-5-yl)-6-(1H-imidazol-1-yl)] quinazoline

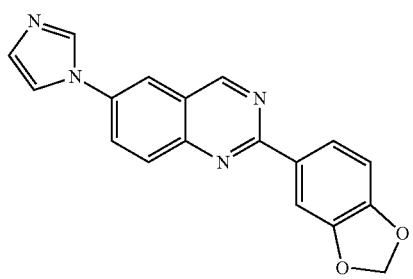

A suspension of 6-amino-2-(1,3-benzodioxol-5-yl)-quinazoline (2.5 g, 9.4 mmol) and 40% aqueous glyoxal (1.1 ml, 9.4 mmol) in methanol (20 ml) was stirred at r.t. for 18 h. NH$_4$Cl (1.0 g, 0.019 mol), 37% aqueous formaldehyde (1.4 ml, 19 mmol) and methanol (200 ml) were added and the mixture was refluxed for 1 h. 85% H$_3$PO$_4$ (1.4 ml) was added and the mixture was heated at reflux for a further 4 h. The solvent was removed and the residue was poured onto water, and basified with aq. NaOH. The precipitate was filtered, washed with water and dissolved in DCM. The product was extracted with aqueous HCl (0.001 N) for three times. The aqueous layers were collected, basified with $Na_2CO_3$ and extracted with chloroform. The organic layer was washed with water and dried over $Na_2SO_4$. The solution was concentrated i.v., and the residue was triturated with diisopropyl ether. The solid was filtered and dried to give the titled product (2.0 g, 29% yield). $C_{18}H_{12}N_4O_2$, MW: 316.32. mp 217-218° C.; $^1$H NMR (DMSO-d6) 9.65 (s, 1H), 8.36-8.50 (m, 3H), 8.14-8.22 (m, 2H), 8.00 (d, 2H), 7.21 (s, 1H), 7.12 (d, 1H), 6.16 (s, 2H); IR (KBr) 1504, 1446, 1251; TLC ($CHCl_3$:MeOH 9:1) Rf=0.30.

6-amino-2-(1,3-benzodioxol-5-yl)-quinazoline

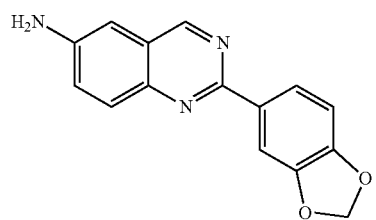

A suspension of 6-nitro-2-(1,3-benzodioxol-5-yl)-quinazoline (37 g, 0.126 mol) and $SnCl_2$ $2H_2O$ (117.2 g, 0.504 mol) in ethanol (500 ml) was heated at reflux for 1 h. After cooling to r.t., the solvent was removed i.v., chloroform was added and the mixture was basified with ammonia. The precipitate was filtered off and washed with chloroform. The filtrates were collected, washed with water and dried over $Na_2SO_4$. The solution was concentrated i.v., and the residue triturated with diisopropyl ether/petroleum ether. The solid was filtered and dried i.v. to give the titled product (21.2 g, 64% yield). $C_{15}H_{11}N_3O_2$, MW: 265.27. mp 191-192° C.; $^1$H NMR (DMSO-d6) 9.24 (s, 1H), 8.05 (dd, 1H), 7.91 (d, 1H), 7.73 (d, 1H), 7.39 (dd, 1H), 7.03 (d, 1H), 6.90 (d, 1H), 6.11 (s, 2H), 5.93 (s, 2H); IR (KBr) 3319, 3203, 1631, 1500, 1446; TLC ($CHCl_3$/MeOH 9/1) Rf=0.3.

6-nitro-2-(1,3-benzodioxol-5-yl)-quinazoline

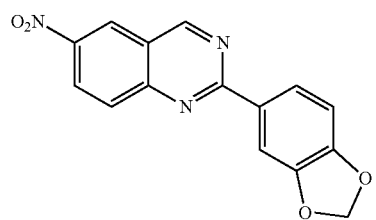

To a suspension of 5-nitro-2-amino-benzylamine hydrochloride (31 g, 0.152 mol) in DCM (450 ml) was added at 0° C. TEA (52.6 ml, 0.38 mol) and a solution of piperonyloyl chloride (27.3 g, 0.16 mol) in DCM (80 ml). The mixture was stirred for 2 hours at r.t. The solvent was removed i.v. and the residue triturated with ethanol/water 1/9, then with diisopropyl ether. The obtained solid was dried and suspended in toluene (900 ml) and $POCl_3$ (670 ml). The mixture was heated at reflux for 2 hours, then the solvent was removed i.v. and the residue was triturated with water/ammonia, washed with water, dried over $P_2O_5$. A mixture of the obtained product and chloranil (32.7 g, 0.129 mol) in toluene (500 ml) was heated at reflux for 2 hours. The mixture was concentrated i.v. and the residue was triturated with NaOH 1M, washed with water and with methanol. The obtained solid was dried i.v. (37 g, 82.5% yield). $C_{15}H_9N_3O_4$, MW: 295.26, mp 220-222° C.

5-nitro-2-amino-benzylamine hydrochloride

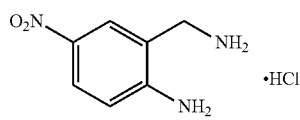

A solution of borane in THF (1 M, 840 ml) was added to a suspension of 5-nitro-anthranilonitrile (120 g, 0.70 mol) in THF (1.2 L) under $N_2$ at 0° C. The mixture was stirred for 2 hours at r.t. After cooling at 0° C., absolute EtOH (400 ml) was added, and HCl was bubbled through the solution. The mixture was concentrated under reduced pressure and the residue was triturated with ethanol, then with diisopropyl ether. The obtained solid was dried in vacuum to give the titled product (140 g, 98.6% yield). $C_7H_9N_3O_2$.HCl, MW: 203.63. TLC ($CHCl_3$:MeOH:$H_2O$:$NH_3$ 85:25:2:1) Rf=0.3.

Example 4

[2-(benzofuran-5-yl)-6-(1H-imidazol-1-yl)]quinazoline dihydrochloride

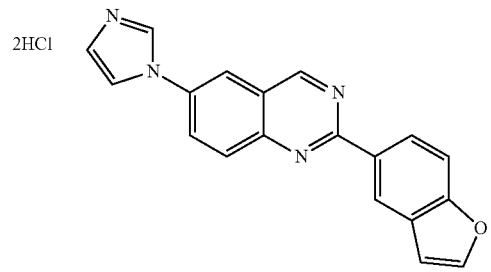

This compound was synthesized in 20% yield starting from 6-amino-2-(5-benzofuran)-quinazoline, according to the procedure described in example 3 for [2-(1,3-benzodioxol-5-yl)-6-(1H-imidazol-1-yl)]quinazoline. $C_{19}H_{12}N_4O$. 2HCl; MW: 385.25; mp 284.7-285.1° C.; $^1$H NMR (DMSO-d6) 10.00 (s, 1H), 9.78 (s, 1H), 8.90 (s, 1H), 8.71 (d, 1H), 8.58 (d, 1H), 8.47 (m, 2H), 8.29 (d, 1H), 8.10 (d, 1H), 8.02 (s, 1H), 7.78 (d, 1H), 7.15 (s, 1H); IR (KBr) 3399, 3097, 1614; TLC ($CHCl_3$:MeOH 9:1) Rf=0.38.

6-amino-2-(5-benzofuran)-quinazoline

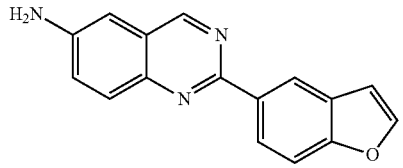

This compound was synthesized in 59% yield starting from benzofurane-5-carboxylic acid, according to the procedure described in example 3 for the synthesis of 6-amino-2-(1,3-benzodioxol-5-yl)-quinazoline. $^1$H NMR (DMSO-d6) 9.31 (s, 1H), 8.77 (s, 1H), 8.48 (dd, 1H), 8.06 (d, 1H), 7.68-7.80 (m, 2H), 7.41 (dd, 1H), 7.10 (d, 1H), 6.93 (d, 1H); TLC (tol/AcOEt 7/3) Rf=0.35.

Synthesis of 6-nitro-2-(5-benzofuran)-quinazoline

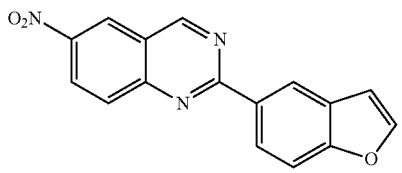

This compound was synthesized in 76% yield, according to the procedure described in example 2 for the synthesis of 6-nitro-2-(1,3-benzodioxol-5-yl)-quinazoline. TLC (tol/AcOEt 7/3) Rf=0.80; mp. 293-7° C.

Example 5

[2-(2,3-dihydro-1,4-benzodioxin-6-yl)-6-(1H-imidazol-1-yl)quinazoline

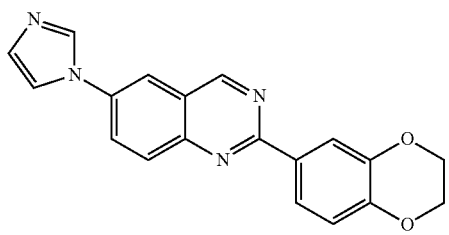

This compound was synthesized in 25% yield, according to the procedure described in example 3 for [2-(1,3-benzodioxol-5-yl)-6-(1H-imidazol-1-yl)]quinazoline. $C_{19}H_{14}N_4O_2$, MW: 330.35; mp 131.5-131.9° C.; $^1$H NMR (DMSO-d6) 9.64 (s, 1H), 8.49 (s, 1H), 8.32-8.43 (m, 2H), 8.18 (s, 1H), 8.03-8.13 (m, 2H), 7.97 (d, 1H), 7.21 (s, 1H), 7.04 (d, 1H), 4.34 (s, 4H); IR (KBr) 1555, 1507, 1286; TLC (CHCl$_3$:MeOH 9:1) Rf=0.38.

6-amino-2-(2,3-dihydro-1,4-benzodioxin-6-yl)-quinazoline

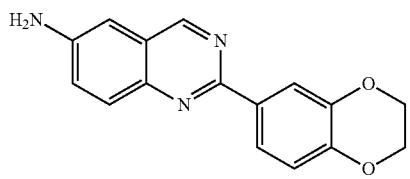

This compound was synthesized in 67% yield, according to the procedure described in example 3 for 6-amino-2-(3,4-methylendioxy-phenyl)-quinazoline. $C_{16}H_{13}N_3O_2$, MW: 279.30. mp 179.4-181.6° C.; $^1$H NMR (DMSO-d6) 9.24 (s, 1H), 7.92-7.98 (m, 2H), 7.72 (d, 1H), 7.38 (dd, 1H), 6.89-6.99 (m, 2H), 5.91 (s, 2H), 4.31 (s, 4H); IR (KBr) 1555, 1507, 1286; TLC (CHCl$_3$/MeOH 9/1) Rf=0.65.

6-nitro-2-(2,3-dihydro-1,4-benzodioxin-6-yl)-quinazoline

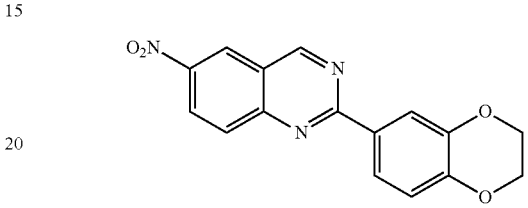

This compound was synthesized in 70% yield, according to the procedure described in example 3 for 6-nitro-2-(3,4-methylendioxy-phenyl)-quinazoline. $C_{16}H_{11}N_3O_4$, MW: 309.28; mp: 263-265; TLC (tol/AcOEt 7/3) Rf=0.80.

Example 6

[2-(3,4-dichlorophenyl)-6-(1H-imidazol-1-yl)]quinazoline

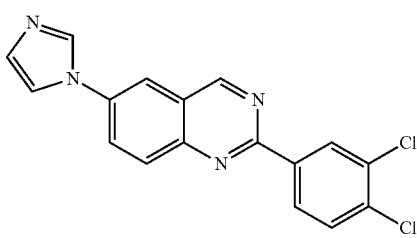

This compound was synthesized in 32% yield, starting from 6-amino-2-(3,4-dichloro-phenyl)-quinazoline (prepared as described in EP1571142), according to the procedure described in example 3 for [2-(1,3-benzodioxol-5-yl)-6-(1H-imidazol-1-yl)]quinazoline. $C_{17}H_{10}Cl_2N_4$, MW: 341.20; mp 131.5-131.9° C.; $^1$H NMR (DMSO-d6) 9.70 (s, 1H), 8.41-8.66 (m, 4H), 8.22 (d, 1H), 7.98 (s, 1H), 7.82 (m, 2H), 7.21 (s, 1H); IR (KBr) 1578, 1548, 1500; TLC (CHCl$_3$:MeOH 9:1) Rf=0.41.

Example 7

[2-[(4-benzyloxy)phenyl-6-(1H-imidazol-1-yl)]quinazoline dihydrochloride

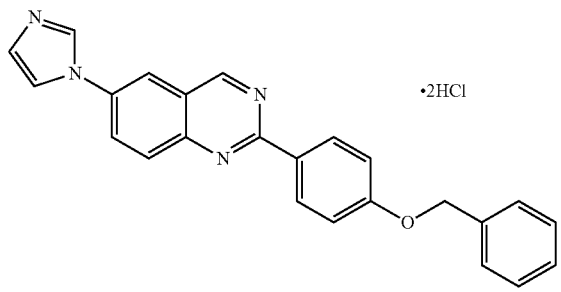

This compound was synthesized in 44% yield, starting from 6-amino-2-(4-benzyloxy-phenyl)-quinazoline, according to the procedure described in example 3 for [2-(1,3-benzodioxol-5-yl)-6-(1H-imidazol-1-yl)]quinazoline. The free base was converted to the hydrochloride salt by treating its methanol suspension with methanol/HCl and evaporating. The solid was triturated in MeCN and dried i.v. to give the titled compound. $C_{24}H_{18}N_4O\cdot2HCl$, MW: 451.36; $^1H$ NMR (DMSO-d6) 9.81 (s, 1H), 8.02-8.96 (m, 7H), 7.21-7.52 (m, 8H), 5.24 (s, 2H) mp 170° C.; IR (KBr) 3399, 2925, 1603, 1512, 1259; TLC ($CHCl_3$:MeOH 9:1) Rf=0.30.

Pharmacological Evaluation of the Compounds of the Invention

The efficacy of the compounds of Formula (I) for the treatment of inflammatory and neuropathic pain along with inflammatory related disorders has been determined using the following in vitro assays and in vivo animal models.

Compounds of the invention are not effective in inhibiting cycloxygenase enzymes (COX-1 and COX-2), since they have been proven not to be effective up to $10^{-5}$ M concentration, in standard in vitro test either for COX-1 or for COX-2 enzyme inhibition. Furthermore compounds of the invention are not effective in inhibiting nitric oxide synthase enzymes, since they have been proven not to be effective up to $10^{-5}$ M concentration, in standard in vitro test for iNOS and nNOS enzyme inhibition. Accordingly, the compounds of the invention are not acting as classical COX or iNOS enzyme inhibitors.

The compounds of the invention have been found effective in interfering with COX-2 and cytokines production, in several cell lines; examples of these effects are reported in Table 3, for COX-2 and IL-1β and IL-6 cytokines, in IL-1 stimulated human chondrosarcoma cell line.

TABLE 3

| Compound | Concentration (μM) | Inhibition (%) of COX-2 production | Inhibition (%) of IL-1 production | Inhibition (%) of IL-6 production |
| --- | --- | --- | --- | --- |
| Example 1 | 0.3 | 20 | 10 | 35 |
| Example 3 | 0.3 | 35 | 20 | 20 |
|  | 1 | 64 | 15 | 35 |
|  | 10 | 75 [(1)] | 40 | NA |
| Example 5 | 0.3 | 50 | 20 | NE |
|  | 1 | 60 | 30 | NE |
|  | 10 | 70 | 40 | 35 |

[(1)] $IC_{50}$ is 0.63 ± 0.24 μM.

To this cytokine modulator property can be ascribed completely or in part the anti-inflammatory and striking analgesic properties displayed by the compounds of the invention in in vivo models of inflammation and pain.

The interplantar injection of Zymosan-induced mechanical hyperalgesia was used as a model of inflammatory pain (Meller, Neuropharmacology, 1994, 33, 1471-1478). In this model, typically a male Sprague-Dawley or Wistar rat (200-250 g) receives an interplantar injection of 3 mg/100 μl zymosan into one hind paw. A marked inflammation occurs in this hind paw. Drugs are administered orally for evaluation of efficacy, 30 min. before the inflammatory insult. The hyperalgesia induced by zymosan administration was evaluated using the Randall-Selitto method (Arch. Int. Pharmacodyn., 1957, 111, 409). The quantitation of the analgesic effect is achieved by an analgesimeter, which consist in applying to the inflamed paw an increasing weight (from 130-140 g up to 500 g). The difference in the mechanical pain threshold between the basal value (generally 230-250 g) and the one tolerated by the animals treated with the drug, determined 4 hours after the inflammatory challenge, is defined as mechanical hyperalgesia. Mechanical hyperalgesia is expressed for the compounds of the invention as $ED_{50}$, which is the dose of the administered compound able to increase the pain threshold by 50% in comparison with the group of control animals. The corresponding $ED_{100}$, representing the dose able of reducing of 100% the pain threshold, can be calculated for those cases where there is a linear dose-response relationship. In vivo anti-inflammatory effect exerted by the compound of the invention can be assessed in the same Zymosan induced inflammation test described above, by measuring the volume of the oedema induced by the inflammatory agent. The oedema was evaluated as the increase in the volume of the Zymosan injected paw within a time of 0-2 hrs. The measurements of the variation of the oedema volume of the paw were recorded using hydroplethysmometer, which consists of two plastic cuvettes containing a surfactant liquid, the larger one being used for immersion of the paw, connected to the smaller one which contains a transducer capable of recording small displacements of the volume used for the measure. The paw is immersed in the cuvettes up to the tibiotarsal joint. The volume of the liquid displaced is proportional to the extent of the inflammation. The efficacy of the compounds of the invention in preventing oedema formation is expressed as $ED_{30}$, is measured 2 hours after the inflammatory challenge, and represents the dose able of reducing of 30%, the Zymosan induced paw volume increase in comparison to control animals (animals treated with Zymosan but treated with only distilled water instead of the testing compound). The corresponding $ED_{50}$, representing the dose able of reducing of 50% the Zymosan induced paw volume increase, can be calculated for those cases where there is a linear dose-response relationship. In both the experiments, for each test compound, at least three doses were used, with 10 animals per group. Compounds of the invention were tested at 10, 20 and 40 mg/Kg.

The performance of representative compounds of Formula (I), in the tests described above, is summarized for both the analgesic effect and the anti-inflammatory effect in Table 4, where the activity of the compounds of the invention is compared with the performance in the same test of well known standards. Representative compounds of the invention demonstrated efficacy superior or comparable to the standards both in a test of analgesia and for anti-inflammatory effects. In addition, compounds of the invention did not display ulcerative side effects comparable to the ones displayed by Nimesulide, even at the higher doses tested.

TABLE 4

| Compound | Analgesia (mg/Kg) ED$_{50}$ | ED$_{100}$ | Oedema ED$_{30}$ | Reduction (mg/Kg) ED$_{50}$ |
|---|---|---|---|---|
| Example 1 | 6.5 | 10 | 7.3 | 97 |
| Example 3 | 2.8 | 5 | 172 | NC |
| Celecoxib | 9 | 1172 | 13.8 | 644 |
| Tramadol | 25.7 | 405 | NE | NE |
| Nimesulide | 7.4 | 161 | 0.5 | 33.4 |

NE: not effective;
NC: not computable

Analgesic activity of the compounds of Formula (I) can be further evaluated in an animal model of chronic inflammatory pain. Since clinically, inflammatory pain is most often associated with chronic conditions such as arthritis and chronic lower back pain, where any inflammation or plastic neuronal change in the peripheral and central nervous system would have been occurring for long time, chronic animal paradigms in which the inflammatory insult has had time to induce centrally mediate changes, may result more predictive. The original model of chronic inflammatory pain was based on injection of inflammatory mediator (adjuvant) into the base of the tail in rats. As a consequence of this treatment, a polyarthritis comprising profound inflammation and hyperalgesia initially at the site of the injection occurs. However, due to T-cell mediated hypersensivity reaction, the disease develops, in a couple of weeks, in multiple joint involvement and subsequent lesions to eyes, ears, nose and genitals. These global effects are not reflecting those clinically observed in common pathologies characterized by chronic inflammatory pain. More recently, it was shown how the use of Complete Freund's Adjuvant (CFA; *Mycobacterium tuberculosis*) as triggering agent for the inflammatory response along with the use of an appropriate protocol can give rise to a more suitable model. CFA-induced prolonged inflammation has been used extensively in studies of behavioural pain response (K. Walker, Mol Med Today, 1999, 5, 319-321) since it has been considered also suitable for studying involvement of neuronal plasticity in chronic pain (R. Sharif Naeini, Eur. J. Neuroscience, 2005, 22, 8, 2005-2015). Experiments are performed as described in the literature (C. J. Woolf, Br. J. of Pharmacology, 1997, 121, 417-424); 8 rats were used for each group, each product was tested at three doses (3, 10, 30 mg/kg), the products were administered i.p., 24 hours after the interplantar challenge, and the analgesic activity was measured starting from the 24 hours following the challenge. In Table 5, results obtained in the CFA model, for representative compounds of Formula (I) are listed in comparison to Piroxicam, a recognized standard. Analgesic effect is assessed using the same equipment as before described for the Randall-Selitto model, results are reported as maximum percent effect (MPE) which represents the difference (%) in pain threshold between the animals treated with the drug and the controls that received only the vehicle (reduction of the nociceptive effect, due to paw loading with increasing weight, in comparison to controls which received CFA treatment). 100% protection means that the animal treated with the compound and CFA can tolerate the same stimulus (weight) as the control animal which has not received CFA treatment. MPE higher than 100% mean that the animal treated with the compound and CFA can tolerate stimuli (weight) higher than the control animals, which has not received CFA treatment (hypoalgesia). From the MPE data at 0.5 hrs, the doses yielding a protection of 50% (ED$_{50}$) and 100% (ED$_{100}$) have been calculated.

TABLE 5

| | | CFA | | | | | | |
|---|---|---|---|---|---|---|---|---|
| Compound | Dose mg/kg | MPE 0.5 hrs. | MPE 1.5 hrs. | MPE 3 hrs. | MPE 6 hrs. | MPE 24 hrs. | ED$_{50}$ 0.5 hrs. mg/kg | ED$_{100}$ |
| Example 1 | 3 | 52 | 4 | NE | NE | NE | 5.5 | 9.6 |
|  | 10 | 67 | 63 | 29 | 22 | 5 |  |  |
|  | 30 | 367 | 368 | 321 | 239 | 60 |  |  |
| Example 3 | 3 | 54 | 90 | 32 | 5 | NE | 2.7 | 4.7 |
|  | 10 | 216 | 188 | 85 | 23 | 3 |  |  |
|  | 30 | 344 | 198 | 101 | 49 | 41 |  |  |
| Piroxicam | 30 | 102 | 111 | 54 | 24 | 38 | NC | NC |

NE: Not Effective;
NC: Not Calculable

The compounds of the invention demonstrated also in this test a pronounced and long lasting analgesic effect, at doses of 10 and 30 mg/Kg, being the highest dose characterized with a remarkable hypoalgesic effect. The calculated ED$_{50}$ and ED$_{100}$ values were lower than 10 mg/kg. At this dose the representative compounds are much more effective than Piroxicam, the reference standard.

Painful diabetic neuropathy is one of the most common complications of insulin-dependent diabetes in man; in particular, diabetes can be associated with neuropathic pain which fails to be treated by classical analgesics. Streptozotocin (STZ)-induced diabetes in the rat has been increasingly used as a model of painful diabetic neuropathy to assess the efficacies of potential analgesic agents (C. Courteix, Pain 1993, 53, 81-8). The compounds of the invention were tested for efficacy in reducing mechanical hyperalgesia associated with STZ-induced diabetes in the rat, according to the experimental model as described by the literature. Diabetes was produced with the injection of a single dose (75 mg/Kg i.p.) of STZ. In the following four weeks after the induction of diabetes the clinical symptoms (weight, body and skin temperature, motility and hyperglycemia) progressively developed by the animals, are strictly monitored. After four weeks, the scores obtained in diabetic rats to various pain stimuli (in particular mechanical stimuli) were greater than those in normal rats, indicating hyperalgesia. The hyperalgesia induced by diabetes was evaluated using the Randall-Selitto method as above described, and quantitated using the analgesimeter. Also in this case, the difference in the mechanical pain threshold between the basal value (generally 230-250 g) and the one tolerated by the animals treated with the drug, is defined as mechanical hyperalgesia. The compounds of the invention were administered i.p. (solution, Tween 80, 10% in saline) at different doses, and mechanical hyperalgesia was measured at the reported time, as maximum percent effect (MPE) which represents the difference (%) in pain threshold between the animals treated with the drug and the controls that received only the vehicle, compared with the weight borne by naïf non-diabetic controls. A 100% protection means that the diabetic animals treated with the compound can tolerate the same stimulus (weight) as the naïf non-diabetic animals. MPE higher than 100% means that the diabetic animal treated with the compound can tolerate stimuli (weight) higher than the control non-diabetic animals (hypoalgesia).

In Table 6, the performance of representative compounds of Formula (I), in the above described model of neuropathic pain, is compared with some known pharmacological standards used for the clinical treatment of this pathology. In particular, from the MPE data at 0.5 hrs, the doses yielding a protection of 50% (ED$_{50}$) and 100% (ED$_{100}$) have been calculated.

TABLE 6

Neuropathic Pain

| Compound | Dose mg/kg | MPE 0.5 hrs. | MPE 1.5 hrs. | MPE 3 hrs. | MPE 6 hrs. | $ED_{50}$ 0.5 hrs mg/kg | $ED_{100}$ |
|---|---|---|---|---|---|---|---|
| Example 1 | 3 | 24 | NE | NE | NE | 5.5 | 9.6 |
| CR4056 | 10 | 41 | 68 | NE | NE | | |
| | 30 | 236 | 225 | 171 | 34 | | |
| Example 3 | 3 | 73 | 88 | 50 | 24 | 2.9 | 5.3 |
| CR4115 | 10 | 141 | 143 | 98 | 49 | | |
| | 30 | 283 | 273 | 263 | 264 | | |
| Gabapentin | 10 | NE | NE | NE | NE | NC | NC |
| | 30 | NE | NE | NE | NE | | |
| | 100 | NE | NE | NE | NE | | |
| | 300 | NE | NE | NE | NE | | |
| Amitriptyline | 3 | 44 | 40 | 5 | NE | NC | NC |
| | 10 | 68 | 77 | NE | NE | | |
| | 30 | 65 | 69 | 23 | NE | | |
| Tramadol | 3 | 26 | 53 | 7 | NE | 10.9 | 251 |
| | 10 | 58 | 48 | 27 | NE | | |
| | 30 | 54 | 64 | 23 | NE | | |
| | 50 | 81 | 60 | 43 | NE | | |

NE: not effective;
NC = not calculable;
*) extrapolated value

Representative Compounds of Formula I demonstrated to be quite effective, especially at the doses of 30 mg/kg (i.e. protection higher than 100%), with $ED_{50}$ and $ED_{100}$ values lower than 10 mg/kg, as in the Zymosan and CFA tests. On the contrary, all of the tested standards exhibited a much lower efficacy, if any, in this paradigm. In fact, an $ED_{50}$ value was calculable only for tramadol (for this standard the $ED_{100}$ was only extrapolated from a dose-response curve approaching the 100% protection).

Pharmaceutical Compositions

Compounds of Formula I can be used in the manufacture of a suitable medication for the therapeutic treatment of pain and inflammatory related disorders. Especially for treatment of chronic pain disorders and immune-driven inflammatory events, which are a significant cause of many chronic inflammatory diseases where prolonged inflammation causes tissue destruction and results in extensive damage.

Accordingly, appropriate pharmaceutical composition of compounds of Formula (I), their salts and solvates thereof can be used for the treatment of acute and chronic pain, including but not limited to inflammatory pain and associated hyperalgesia and allodynia, osteoarthritis pain, postoperative pain, visceral pain, pain associated with cancer, trigeminal neuralgia, acute herpetic and post herpetic neuralgia, neuropathic pain, diabetic neuropathy.

In addition, appropriate pharmaceutical composition of compounds of Formula (I), their salts and solvates thereof, can be used for the treatment of immune-driven inflammatory events including but not limited to arthritis, rheumatoid arthritis and osteoarthritis, inflammatory disorders of the gastrointestinal tract such as inflammatory bowel disease (IBD), ulcerative colitis, Crohn's disease (CD), inflammatory urinary bladder disorders, inflammatory disorders of the respiratory tract chronic obstructive pulmonary disease (COPD) and asthma, post operative inflammatory complications, inflammatory eyes disorders, systemic lupus erythematosus, skin diseases such as eczema, psoriasis and dermatitis.

In addition, appropriate pharmaceutical composition of compounds of Formula (I), their salts and solvates thereof, can be used for the treatment of cancer, including but not limited to: colon cancer, multiple myeloma, breast, cervical, prostate and lung cancer.

The compounds of the present invention may be administered orally, parenterally or topically,
in a pharmacological effective amount. The term parenteral used herein includes intravenous, intramuscular, subcutaneous, intra-dermal and intra-articular.

For all methods of treatment herein discussed for the compounds of Formula (I), the daily oral dosage regimen will preferably be from about 0.1 to about 20 mg/Kg of total body weight. It will also be recognised by one of skill in the art that the optimal quantity and spacing of individual dosages of a compound of Formula (I) will be determined by the nature and extent of the condition being treated.

This invention also relates to a composition suitable for the treatment of the above diseases, containing a pharmaceutically effective amount of a compound of Formula (I), its salts, solvates and prodrugs thereof and its pharmaceutically acceptable carrier or diluent.

In order to use a compound of Formula (I) in therapy, it will normally be formulated into a dosage form in accordance with conventional methods of pharmacy and current guidelines and relevant good laboratory and manufacturing practices.

The preferred route of administration for the compounds of the invention is oral. The compounds of the invention can be formulated in a wide variety of oral dosage forms, such as capsules, tablets, pills, powders and dispersible granules. Suitable carriers can be one or more substances which may also act as diluents, flavouring agents, solubilizer, lubricants, suspending agents, binders.

Suitable carriers include but are not limited to magnesium carbonate, magnesium stearate, talc, lactose, pectin, dextrin, starch, methylcellulose, sodium carboxymethyl cellulose, cocoa butter and the like. Techniques used to prepare oral formulations are the conventional mixing, granulation and compression or capsules filling. Other forms suitable for oral administration include emulsions, syrups and aqueous solutions. Emulsions can be prepared using emulsifying agents for example lecithin, propylene glycol or sorbitan monooleate. Aqueous solutions can be prepared by dissolving the active component in water and adding suitable colorants, flavours, stabilising agents.

The compounds of the present invention may be formulated for parenteral administration (e.g., by injection or by continuous infusion) as a composition with suitable carriers including aqueous vehicles solutions (i.e.: saline, dextrose) or and/or oily emulsions. The drug product may be presented in unit dose forms, for example in ampoules or pre-filled syringes.

Formulation suitable for topical administration include liquid or semi-liquid preparations suitable for the penetration through the skin (e.g.: liniments, lotions, ointments, creams and pastes) and drops suitable for administration to the eyes.

The invention claimed is:
1. A method for the pharmacological treatment of neuropathic and inflammatory pain, comprising administering, to a subject in need thereof, an effective amount of a compound of Formula (I):

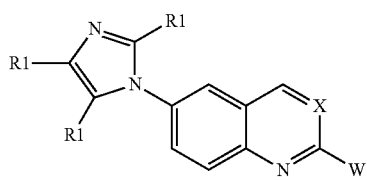

wherein:
X is a nitrogen atom;
W is independently selected from an aryl group or an heteroaryl group of Formula II:

Group of Formula II:

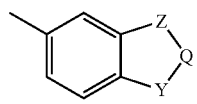

when W is an aryl group, it is an unsubstituted phenyl of or phenyl substituted with one or more substituents independently selected from halogen (—F, —Cl, —Br), trifluoromethyl (—CF$_3$), alkyl, hydroxyl (—OH), alkoxy, trifluoromethoxy (—OCF$_3$), cyano (—CN), carboxamido (—CONHR$_3$ or —NHCOR$_3$ or —CONR$_2$R$_3$), carbonyl (—CO—R$_3$), alkylthio (—SR$_3$), sulfonyl (—SOR$_3$) and sulfonyl (—SO$_2$R$_3$), wherein R$_2$ and R$_3$ groups are as defined below;

when W is an heteroaryl group of Formula II, it is a benzocondensed-5 or -6 membered heterocycle, wherein:
Z and Y are independently selected from: an oxygen atom (—O—), a sulphur atom (—S—), or the groups: —SO$_2$—, —CHR$_3$—, —CR$_3$=, —NH—, —N=;
Q is independently selected from the groups: —CHR$_3$—, —CH=, —CR$_3$=, —CHR$_3$—CH$_2$—;
provided that the combination of Y, Z, Q groups give rise to: 1,3-benzodioxole, 1,3-benzodithiol, benzofuran, 2,3-dihydrobenzofuran, benzothiophene, 2,3-dihydrobenzothiophene, 2,3-di-hydrobenzothiophene S,S-dioxide, indole, 2,3-dihydroindole, benzimidazole, benzoxazole, benzothiazole, 2H-3,4-dihydrobenzopyran, 2H-3,4-dihydrobenzothiopyran, 2H-3,4-dihydrobenzothiopyran S,S-dioxide, 2,3-dihydro-[1,4]-benzodioxine (1,4-benzodioxan), 2,3-dihydro-[1,4]-benzothiazine, 2,3-dihydro-[1,4]-benzothiazine S,S-dioxide, [2,3-dihydro-[1,4]-benzoxazine;
R1 is independently selected from hydrogen (—H) or C$_1$-C$_4$ alkyl or hydroxymethyl (—CH$_2$OH), aminomethyl (—CH$_2$NH$_2$), dimethylaminomethyl (—CH$_2$NMe$_2$), trifluoromethyl (—CF$_3$); the C$_1$-C$_4$ alkyl group is a linear or branched hydrocarbon chain; provided that in compounds of Formula (I) not more than two R1 groups are simultaneously C$_1$-C$_4$ alkyl or trifluoromethyl (—CF$_3$) and only one R1 group is hydroxymethyl (—CH$_2$OH), aminomethyl (—CH$_2$NH$_2$) or dimethylaminomethyl (—CH$_2$NMe$_2$);
R$_2$ is independently selected from C$_1$-C$_6$ alkyl or aryl; C$_1$-C$_6$ alkyl is a linear or branched, saturated or unsaturated C$_1$-C$_6$ hydrocarbon chain, optionally substituted with an aryl, aryl being as defined above;
R$_3$ is independently selected from hydrogen, C$_1$-C$_6$ alkyl and aryl; C$_1$-C$_6$ alkyl is a linear or branched, saturated or unsaturated C$_1$-C$_6$ hydrocarbon chain optionally substituted with an aryl, aryl being as defined above, or a pharmaceutically acceptable salt thereof.

2. The method according to claim 1, wherein the compound of Formula (I) is a compound in which the substituent X is a nitrogen atom and W is an unsubstituted phenyl or phenyl substituted with one or more substituents independently selected from: halogen (—F, —Cl, —Br), trifluoromethyl (—CF$_3$), alkyl, hydroxyl (—OH), alkoxy, trifluoromethoxy (—OCF$_3$), cyano (—CN), carboxamido (—CONHR$_3$ or —NHCOR$_3$ or —CONR$_2$R$_3$), carbonyl (—CO—R$_3$), alkylthio (—SR$_3$), sulfinyl (—SOR$_3$) and sulfonyl (—SO$_2$R$_3$), wherein R$_2$ and R$_3$ are as defined in claim 1.

3. The method according to claim 1, wherein the compound of Formula (I) is a compound in which the substituent X is a nitrogen atom and W is an heteroaryl group of Formula II, wherein the combination of Y, Z, Q groups give rise to: 1,3-benzodioxole, benzofuran, 2,3-dihydrobenzofuran, 2H-3,4-dihydrobenzopyran, 2,3-dihydro-[1,4]-benzodioxine (1,4-benzodioxan).

4. The method according to claim 1, wherein the compound of Formula (I) is a compound in which the substituent X is a nitrogen atom and W is an heteroaryl group of Formula II, wherein the combination of Y, Z, Q groups give rise to: 1,3-benzodithiol, benzothiophene, 2,3-dihydrobenzothiophene, 2,3-dihydrobenzothiophene S,S-dioxide, 2H-3,4-dihydrobenzothiopyran, 2H-3,4-dihydrobenzothiopyran S,S-dioxide.

5. The method according to claim 1, wherein the compound of Formula (I) is a compound in which the substituent X is a nitrogen atom and W is an heteroaryl group of Formula II, and wherein combination of Y, Z, Q groups give rise to: indole, 2,3-dihydroindole, benzimidazole, benzoxazole, benzothiazole, 2,3-dihydro-[1,4]-benzothiazine, 2,3-dihydro-[1,4]-benzothiazine S,S-dioxide, 2,3-dihydro-[1,4]-benzoxazine.

6. The method according to claim 1, wherein the compound of Formula (I) is in the form of a pharmaceutically acceptable salt selected from the group consisting of hydrochloride, hydrobromide, hydrogensulphate and sulphate, maleate, fumarate, oxalate, methanesulfonate, succinate, ascorbate, tartrate.

7. A method for the pharmacological treatment of acute and chronic pain selected from neuropathic and inflammatory pain, comprising administering, to a subject in need thereof, an effective amount of a compound of Formula (I):

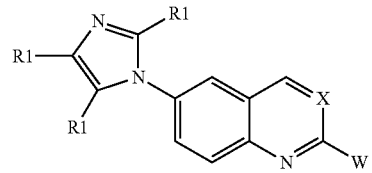

wherein:
X is a nitrogen atom;
W is independently selected from an aryl group or an heteroaryl group of Formula II:

Group of Formula II:

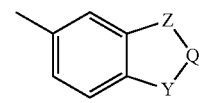

when W is an aryl group, it is an unsubstituted phenyl of or phenyl substituted with one or more substituents independently selected from halogen (—F, —Cl, —Br), trifluoromethyl (—CF$_3$), alkyl, hydroxyl (—OH), alkoxy, trifluoromethoxy (—OCF$_3$), cyano (—CN), carboxamido (—CONHR$_3$ or —NHCOR$_3$ or —CONR$_2$R$_3$), carbonyl (—CO—R$_3$), alkylthio (—SR$_3$), sulfinyl (—SOR$_3$) and sulfonyl (—SO$_2$R$_3$), wherein R$_2$ and R$_3$ groups are as defined below;

when W is an heteroaryl group of Formula II, it is a benzocondensed-5 or -6 membered heterocycle, wherein:

Z and Y are independently selected from: an oxygen atom (—O—), a sulphur atom (—S—), or the groups: —SO$_2$—, —CHR$_3$—, —CR$_3$=, —NH—, —N=;

Q is independently selected from the groups: —CHR$_3$—, —CH=, —CR$_3$=, —CHR$_3$—CH$_2$—; provided that the combination of Y, Z, Q groups give rise to: 1,3-benzodioxole, 1,3-benzodithiol, benzofuran, 2,3-dihydrobenzofuran, benzothiophene, 2,3-dihydrobenzothiophene, 2,3-di-hydrobenzothiophene S,S-dioxide, indole, 2,3-dihydroindole, benzimidazole, benzoxazole, benzothiazole, 2H-3,4-dihydrobenzopyran, 2H-3,4-dihydrobenzothiopyran, 2H-3,4-dihydrobenzothiopyran S,S-dioxide, 2,3-dihydro-[1,4]-benzodioxine (1,4-benzodioxan), 2,3-dihydro-[1,4]-benzothiazine, 2,3-dihydro-[1,4]-benzothiazine S,S-dioxide, [2,3-dihydro-[1,4]-benzoxazine;

R1 is independently selected from hydrogen (—H) or C$_1$-C$_4$ alkyl or hydroxymethyl (—CH$_2$OH), aminomethyl (—CH$_2$NH$_2$), dimethylaminomethyl (—CH$_2$NMe$_2$), trifluoromethyl (—CF$_3$); the C$_1$-C$_4$ alkyl group is a linear or branched hydrocarbon chain; provided that in compounds of Formula (I) not more than two R1 groups are simultaneously C$_1$-C$_4$ alkyl or trifluoromethyl (—CF$_3$) and only one R1 group is hydroxymethyl (—CH$_2$OH), aminomethyl (—CH$_2$NH$_2$) or dimethylaminomethyl (—CH$_2$NMe$_2$);

R$_2$ is independently selected from C$_1$-C$_6$ alkyl or aryl; C$_1$-C$_6$ alkyl is a linear or branched, saturated or unsaturated C$_1$-C$_6$ hydrocarbon chain, optionally substituted with an aryl, aryl being as defined above;

R$_3$ is independently selected from hydrogen, C$_1$-C$_6$ alkyl and aryl; C$_1$-C$_6$ alkyl is a linear or branched, saturated or unsaturated C$_1$-C$_6$ hydrocarbon chain optionally substituted with an aryl, aryl being as defined above, or a pharmaceutically acceptable salt thereof.

8. The method according to claim 7, wherein the compound of Formula (I) is a compound in which the substituent X is a nitrogen atom and W is an unsubstituted phenyl or phenyl substituted with one or more substituents independently selected from: halogen (—F, —Cl, —Br), trifluoromethyl (—CF$_3$), alkyl, hydroxyl (—OH), alkoxy, trifluoromethoxy (—OCF$_3$), cyano (—CN), carboxamido (—CONHR$_3$ or —NHCOR$_3$ or —CONR$_2$R$_3$), carbonyl (—CO—R$_3$), alkylthio (—SR$_3$), sulfinyl (—SOR$_3$) and sulfonyl (—SO$_2$R$_3$), wherein R$_2$ and R$_3$ are as defined in claim 1.

9. The method according to claim 7, wherein the compound of Formula (I) is a compound in which the substituent X is a nitrogen atom and W is an heteroaryl group of Formula II, wherein the combination of Y, Z, Q groups give rise to: 1,3-benzodioxole, benzofuran, 2,3-dihydrobenzofuran, 2H-3,4-dihydrobenzopyran, 2,3-dihydro-[1,4]-benzodioxine (1,4-benzodioxan).

10. The method according to claim 7, wherein the compound of Formula (I) is a compound in which the substituent X is a nitrogen atom and W is an heteroaryl group of Formula II, wherein the combination of Y, Z, Q groups give rise to: 1,3-benzodithiol, benzothiophene, 2,3-dihydrobenzothiophene, 2,3-dihydrobenzothiophene S,S-dioxide, 2H-3,4-dihydrobenzothiopyran, 2H-3,4-dihydrobenzothiopyran S,S-dioxide.

11. The method according to claim 7, wherein the compound of Formula (I) is a compound in which the substituent X is a nitrogen atom and W is an heteroaryl group of Formula II, and wherein combination of Y, Z, Q groups give rise to: indole, 2,3-dihydroindole, benzimidazole, benzoxazole, benzothiazole, 2,3-dihydro-[1,4]-benzothiazine, 2,3-dihydro-[1,4]-benzothiazine S,S-dioxide, 2,3-dihydro-[1,4]-benzoxazine.

12. The method according to claim 7, wherein the compound of Formula (I) is in the form of a pharmaceutically acceptable salt selected from the group consisting of hydrochloride, hydrobromide, hydrogensulphate and sulphate, maleate, fumarate, oxalate, methanesulfonate, succinate, ascorbate, tartrate.

* * * * *